United States Patent [19]

Kubo et al.

[11] 4,186,200
[45] Jan. 29, 1980

[54] NOVEL FUSED DERIVATIVES OF 2-PYRIDONES

[75] Inventors: Kazuo Kubo, Urawa; Noriki Ito, Iwatsuki; Isao Souzu, Urawa; Yasuo Isomura, Yokohama; Hiroshige Homma, Omiya; Masuo Murakami, Tokyo, all of Japan

[73] Assignee: Yamanouchi Pharmaceutical Co., Ltd., Tokyo, Japan

[21] Appl. No.: 876,517

[22] Filed: Feb. 9, 1978

Related U.S. Application Data

[63] Continuation-in-part of Ser. No. 814,325, Jul. 11, 1977, abandoned.

[30] Foreign Application Priority Data

Jul. 22, 1976 [JP] Japan .................................. 51-87486
Dec. 29, 1976 [JP] Japan ................................. 51-158228
Jan. 5, 1977 [JP] Japan ..................................... 51-464
Mar. 31, 1977 [JP] Japan ................................. 52-36384
Apr. 13, 1977 [JP] Japan ................................. 52-42423

[51] Int. Cl.² .................. A61K 31/415; C07D 471/04
[52] U.S. Cl. ..................................... 424/256; 424/251; 544/283; 546/271; 546/274; 546/291
[58] Field of Search .................. 260/296 H; 424/263, 424/256, 251; 546/271, 274

[56] References Cited

U.S. PATENT DOCUMENTS 3,334,099  8/1967  Houlihan .................... 260/239.3 B X Primary Examiner—John D. Randolph
Attorney, Agent, or Firm—Burgess, Ryan and Wayne

[57] ABSTRACT

Novel nitrogen-containing heterocyclic compounds shown by the formula

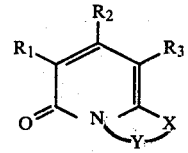

wherein one of $R_1$ and $R_2$ represents a lower alkyl group, a phenyl group, a halophenyl group, or a lower alkoxyphenyl group and the other of them represents a hydrogen atom, a lower alkyl group, or a phenyl lower alkyl group; said $R_1$ and $R_2$ may combine with each other to form a trimethylene group or a tetramethylene group; $R_3$ represents a hydrogen atom, a lower alkyl group, a phenyl group, or a phenyl lower alkyl group; X represents an oxygen atom, a sulfur atom, an imino group, or a group shown by

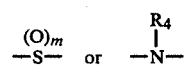

wherein m represents 1 or 2 and $R_4$ represents a lower alkyl group, a hydroxy lower alkyl group, a cycloalkyl group or a phenyl lower alkyl group; and Y represents an ethylene group which may be substituted by lower alkyl group, a trimethylene group, a tetramethylene group, a vinylene group which may be substituted by a lower alkyl group, or

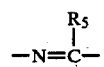

wherein $R_5$ represents a hydrogen atom, a lower alkyl group, a trifluoromethyl group, or a phenyl group; said X is the group shown by

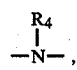

when one of said $R_1$ and $R_2$ is a lower alkyl group and the other is a hydrogen atom, and said Y is an ethylene group, and the pharmacologically acceptable non-toxic salts thereof. The compounds described above are strong analgesic anti-inflammatory agents.

21 Claims, No Drawings

NOVEL FUSED DERIVATIVES OF 2-PYRIDONES

This application is a continuation-in-part of U.S. patent application Ser. No. 814,325, filed July 11, 1977, now abandoned.

DETAILED DESCRIPTION OF THE INVENTION

The present invention relates to novel nitrogen-containing heterocyclic compounds. More particularly, the invention relates to the nitrogen-containing heterocyclic compounds shown by Formula I

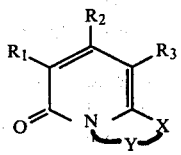

wherein one of $R_1$ and $R_2$ represents a lower alkyl group, a phenyl group, a halophenyl group, or a lower alkoxyphenyl group and the other of them represents a hydrogen atom, a lower alkyl group, or a phenyl lower alkyl group; said $R_1$ and $R_2$ may combine with each other to form a trimethylene group or a tetramethylene group; $R_3$ represents a hydrogen atom, a lower alkyl group, a phenyl group, or a phenyl lower alkyl group; X represents an oxygen atom, a sulfur atom, an imino group, or a group shown by

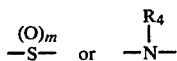

(wherein m is 1 or 2 and $R^4$ represents a lower alkyl group, a hydroxy lower alkyl group, a cycloalkyl group or a phenyl lower alkyl group); and Y represents an ethylene group which may be substituted by a lower alkyl group, a trimethylene group, a tetramethylene group, a vinylene group which may be substituted by lower alkyl group, or

(wherein $R_5$ represents a hydrogen atom, a lower alkyl group, a trifluoromethyl group, or a phenyl group); said X is the group shown by

when one of said $R_1$ and $R_2$ is a lower alkyl group and the other is a hydrogen atom, and said Y is an ethylene group, and the pharmacologically acceptable non-toxic salts thereof.

The compounds of this invention shown by formula I have very strong anti-inflammatory activity and also strong analgesic activity, and hence are novel and useful compounds expected as strong analgesic anti-inflammatory agents.

The definitions of the terms used in the specification and the claims of this invention are as follows:

That is, "lower alkyl group" is a straight or branched chain alkyl group having 1–6 carbon atoms and includes, for example, a methyl group, an ethyl group, a propyl group, an isopropyl group, a n-butyl group, an isobutyl group, a sec-butyl group, a tert-butyl group, an amyl group, an isoamyl group, and a n-hexyl group. "Lower alkoxy group" is a straight or branched chain alkoxy group having 1–6 carbon atoms and includes, for example, a methoxy group, an ethoxy group, a propoxy group, an isopropoxy group, a n-butoxy group, an amyloxy group, and a n-hexyloxy group. "Cycloalkyl group" is a cycloalkyl group having 5–7 carbon atoms and includes a cyclopentyl group, a cyclohexyl group, and a cycloheptyl group. "Halogen atom" includes a fluorine atom, chlorine atom, bromine atom, and an iodine atom. "Phenyl lower alkyl group" is a lower alkyl group substituted by a phenyl group and includes, for example, a benzyl group and a phenethyl group.

The compounds I of this invention have a feature of chemical structure in the point that the 1-position and the 6-position of 2-pyridone are cyclized by a heteroatom and alkylene group and it has not hitherto been known that such nitrogen-containing heterocyclic compounds have excellent anti-inflammatory activity. In addition, in regard to such nitrogen-containing heterocyclic compounds, 7-methyl-5-oxo-, 7,8-dimethyl-5-oxo- and 7-methyl-8-phenyl-5-oxo-1,2,3,5-tetrahydroimidazo[1,2-a]pyridine are described in "Yakugaku Zasshi"; 91(11), 1174–1177(1971) and also 7-methyl-5-oxo-2,3,5-trihydrothiazolo[3,2-a]pyridine is disclosed in "Chem. Ber."; 86, 468(1953). However, the use of these compounds as medicaments is not reported in this literature.

The preferred compounds of this invention are the nitrogen-containing heterocyclic compounds of formula I wherein one of $R_1$ and $R_2$ represents a lower alkyl group, a phenyl group, a halophenyl group or a lower alkoxyphenyl group and the other of them represents a hydrogen atom or a lower alkyl group; said $R_1$ and $R_2$ may combine with each other to form a trimethylene grop or a tetramethylene group; $R_3$ represents a hydrogen atom; X represents an oxygen atom, a sulfur atom, an imino group,

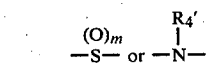

(wherein m represents 1 or 2 and $R_4'$ represents a lower alkyl group, a cycloalkyl group or a phenyl lower alkyl group); and Y represents an ethylene group which may be substituted by a lower alkyl group, a trimethylene group, a tetramethylene group, or a vinylene group which may be substituted by a lower alkyl group; said X is the group shown by

when one of said $R_1$ and $R_2$ is a lower alkyl group and the other of them is a hydrogen atom and said Y is an ethylene group.

One example of the more preferred compounds of the above-described preferred compounds is the nitrogen-containing heterocyclic compounds of formula I wherein $R_1$ and $R_3$ are hydrogen atoms; $R_2$ is a phenyl group, a halophenyl group, or a lower alkoxyphenyl group; X is an imino group or the group shown by

and Y is an ethylene group or a trimethylene group. Another example of the more preferred homologues in the nitrogen-containing heterocyclic compounds of formula I wherein one of $R_1$ and $R_2$ is a phenyl group and the other of them is a hydrogen atom; $R_3$ is a hydrogen atom; X is the group shown by

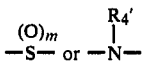

(wherein m is 1 or 2 and $R_4'$ is a lower alkyl group); and Y is an ethylene group; said X is the group shown by

when $R_1$ is a phenyl group and $R_2$ is a hydrogen atom.

A further example of the more preferred compounds is the nitrogen-containing heterocyclic compounds of formula I wherein $R_1$ and $R_3$ are hydrogen atoms; $R_2$ is a lower alkyl group; X is an imino group or the group shown by

(wherein $R_4'$ is a lower alkyl group); and Y is an ethylene group or a trimethylene group; said X is the group shown by

when Y is an ethylene group.

A still further example of the more preferred compounds is the nitrogen-containing heterocyclic compounds of formula I wherein $R_1$ and $R_2$ combine with each other to form a trimethylene group or a tetramethylene group; $R_3$ is a hydrogen atom; X is an oxygen atom, a sulfur atom, an imino group, or the group shown by

(wherein $R_4'$ is a lower alkyl group) and Y is an ethylene group or a trimethylene group. Still another example of the more preferred compounds is the nitrogen-containing heterocyclic compounds of formula I wherein one of $R_1$ and $R_2$ is a phenyl group and the other of them is a lower alkyl group; $R_3$ is a hydrogen atom; X is the group shown by

and Y is an ethylene group, a trimethylene group, or a tetramethylene group. Another example of the more preferred compounds is the nitrogen-containing heterocyclic compounds of formula I wherein one of $R_1$ and $R_2$ is a lower alkyl group, a phenyl group, a halophenyl group or a lower alkoxyphenyl group, and the other of them is a hydrogen atom or a lower alkyl group, said $R_1$ and $R_2$ may combine each other to form a trimethylene group or a tetramethylene group; $R_3$ is a hydrogen atom; X is an oxygen atom, a sulfur atom, an imino group or the group shown by

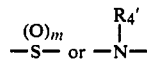

wherein m represents 1 or 2 and $R_4'$ is a lower alkyl group, a cycloalkyl group or a phenyl lower alkyl group; Y is an ethylene group substituted by a lower alkyl group or a vinylene group which may be substituted by a lower alkyl group.

Examples of the particularly preferred compounds of this invention are 5-oxo-7-phenyl-1,2,3,5-tetrahydroimidazo[1,2-a]pyridine, 1-methyl-6-oxo-8-phenyl-1,2,3,4,6-pentahydropyrido[1,2-a]pyrimidine and 1,7-dimethyl-5-oxo-1,2,3,5-tetrahydroimidazo[1,2-a]pyridine.

As the pharmacologically acceptable non-toxic salts of the compounds of this invention shown by formula I, there are the addition salts with an acid such as hydrochloric acid, hydrobromic acid, sulfuric acid, nitric acid, phosphoric acid, etc.

The compounds of this invention shown by formula I are prepared;

(a) by reacting the 2-pyridone derivative shown by formula II

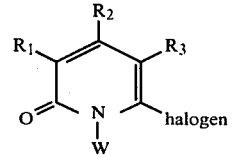

wherein $R_1, R_2$ and $R_3$ have the same meaning as above and W represents a hydrogen atom, a phenyl group, a halophenyl group, a trifluoromethylphenyl group, or a lower alkylphenyl group, with the amine derivative shown by formula III $NH_2—Y—X—H$    III wherein X and Y have the same meaning as above;

(b) by reacting the compound shown by formula IV

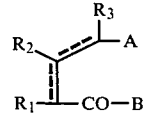

wherein $R_1$, $R_2$ and $R_3$ have the same meaning as above; A represents a cyano group or a carboxy group; B represents a halogen atom, a hydroxyl group or a lower alkoxy group; and the dotted lines show that one of them is a double bond; said B represents a hydroxyl group when said A is a carboxy group, with the amine derivative shown by formula III $NH_2—Y—X—H$    III wherein X and Y have the same meaning as above; or (c) by heating the 2-pyridone derivative shown by formula V

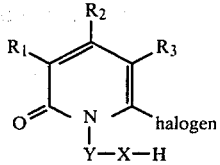

wherein $R_1$, $R_2$, $R_3$, X and Y have the same meaning as above, in the presence of a base.

Practically speaking, process (a) is carried out by reacting the compound of formula II with an equimolar amount or an excessive amount of the compound of formula III in an organic solvent which does not participate in the reaction, such as methanol, ethanol, 2-ethoxyethanol, diglyme, dichlorobenzene, xylene, dimethylformamide, etc. The reaction is performed with heating, that is, performed at a temperature of about the boiling point of the solvent used or at a temperature above the boiling point of the solvent in a sealed tube, but, preferably performed under refluxing with heating. This reaction may be performed in the presence of a base such as potassium carbonate, sodium carbonate, potassium hydrogencarbonate, sodium hydrogencarbonate, etc. Furthermore, the compound of formula III may be supplied to the reaction system as an addition salt with an acid such as acetic acid, etc.

Process (b) is performed by reacting the compound of formula IV with an equimolar amount or an excessive amount of the compound of formula III in an organic solvent which does not participate in the reaction, such as methanol, ethanol, ether, 2-ethoxyethanol, diglyme, xylene, ethyleneglycol, dichlorobenzene, etc. The reaction is preferably performed with heating, that is, performed at a temperature of about the boiling point of the solvent used or at a temperature above the boiling point of the solvent in a sealed tube. The reaction is usually performed under refluxing with heating. Also, the compound of formula III may be supplied to the reaction system as the acid addition salt with an acid such as acetic acid, etc.

Process (c) is performed by heating the compound of formula V in an organic solvent which does not participate in the reaction, such as methanol, ethanol, ether, 2-ethoxyethanol, diglyme, dichlorobenzene, xylene, dimethylformamide, etc., in the presence of a base. The reaction is performed with heating, that is, performed at a temperature of about the boiling point of the solent used or at a temperature above the boiling point of the solvent in a sealed tube. The reaction is preferably performed under refluxing with heating. The reaction is performed in the presence of a base such as sodium hydride, sodium methoxide, sodium ethoxide, potassium carbonate, sodium carbonate, potassium hydrogencarbonate, sodium hydrogencarbonate, etc.

Now, the compounds I of this invention wherein X is the group shown by $$-\underset{}{\overset{(O)_m}{S}}-$$

and Y is an ethylene group which may be substituted by lower alkyl group or a vinylene group which may be substituted by lower alkyl group, that is, the compounds of this invention shown by formula Ia

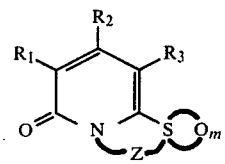

wherein $R_1$, $R_2$, $R_3$, and m have the same meaning as above and Z represents an ethylene group which may be substituted by lower alkyl group of a vinylene group which may be substituted by lower alkyl group, are produced by oxidizing the compounds shown by formula Ib

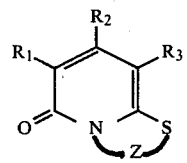

wherein $R_1$, $R_2$, $R_3$, and Z have the same meaning as above. Practically speaking, the reaction is performed by dissolving the compound of formula Ib in an acid such as acetic acid, etc., and oxidizing the compounds with an oxidizing agent such as hydrogen peroxide at room temperature or under heating. Hydrogen peroxide is usually used as a 10-30% aqueous hydrogen peroxide solution. In this case, by properly selecting the reaction conditions such as the reaction time, the reaction temperature, the amount of the oxidizing agent used, etc., the desired monoxide compound (m=1) or the desired dioxide compound (m=2) can be obtained.

Also, the compounds of this invention shown by formula I wherein X is a sulfur atom and Y is a vinylene group which may be substituted by lower alkyl group, that is, the compounds of this invention shown by formula Ic

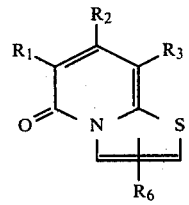

wherein $R_1$, $R_2$ and $R_3$ have the same meaning as above and $R_6$ represents a hydrogen atom or a lower alkyl group, can be produced by reacting the compound shown by formula Id

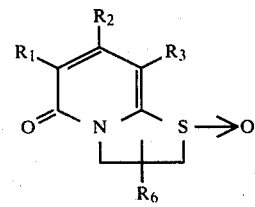

wherein $R_1$, $R_2$, $R_3$, and $R_6$ have the same meaning as above with an acylating agent such as acetic anhydride, etc., to form the compound shown by formula Ie

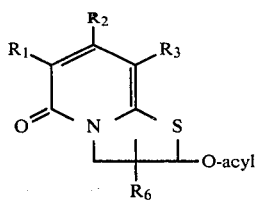

wherein $R_1$, $R_2$, $R_3$, and $R_6$ have the same meaning as above and then treating the compound of formula Ie with an acid. The acid treatment can be performed at room temperature using an acid such as concentrated sulfuric acid, phosphoric acid, etc. In this case, a solvent such as ethanol, etc., may be used.

Furthermore, the compounds of this invention shown by formula I wherein X is the group shown by

that is, the compounds of this invention shown by formula If

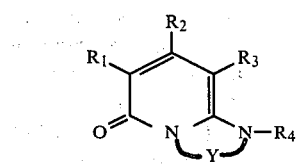

wherein $R_1$, $R_2$, $R_3$, $R_4$ and Y have the same meaning as above, can be produced by reacting the compound shown by formula Ig

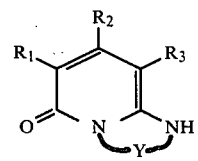

wherein $R_1$, $R_2$, $R_3$ and Y have the same meaning as above, with an equimolar amount or excessive amount of the compound shown by formula IV halogen—$R_4$      VI wherein $R_4$ has the same meaning as above, in an organic solvent which does not participate in the reaction, such as methanol, ethanol, isopropanol, 2-ethoxy ethanol, diglyme, dimethylformamide, etc. This reaction is preferably performed in the presence of a base such as potassium carbonate, sodium carbonate, potassium hydroxide, sodium hydroxide, etc. In the case of using such a base, it is suitable to use a aqueous organic solvent as the reaction solvent. Also, the reaction can be performed in the presence of a base such as sodium hydride, sodium methoxide, sodium ethoxide, etc., and in the case of using such a base, the reaction is usually performed in an organic solvent such as dimethylformamide, etc., as the reaction solvent. Furthermore, the reaction may proceed without heating but the reaction is usually performed with heating.

The compounds of this invention shown by formula I can be produced by the various methods as described above but as shown in the examples described below, they can also be produced by other methods than above.

The compounds of this invention shown by formula I thus produced can be isolated and purified by an ordinary chemical operation such as concentration, recrystallization, column chromatography, etc.

Then, the results of the following experiments show the excellent therapeutical activities of the compounds of this invention:

(a) Carrageenin-induced edema

Male Wister rats (weighting 130–170 g.), one group being 6 rats, fasted overnight were used. According to Wister's method [Proc. Soc. Exp. Biol. Med., 111,544 (1962)], 0.1 ml. of 1% Carrageenin [Iwai Kagaku Yakuhin K.K. Seakem] suspension in 0.9% saline was injected into the plantar tissue of the left hind paw. After 3 hours, each rat was sacrificed by chloroform and the hind paw was cut and weighed immediately. By using the value obtained by subtracting the weight of the untreated hind paw from the weight of the hind paw having injected therein the Carrageenin as the weight of edema, the inhibitory ratio of the sample administered rat groups to control groups was calculated. The sample was orally administered one hour before the injection of Carrageenin. The results obtained are shown in Table 1.

(b) Whittle's method (British J. Pharmacol.; 22, 246–253 (1964))

Male ICR-Mice (weighting 25–35 g.), one group being 12 mice, fasted overnight were used in this test. The sample was orally administered, and 20 minutes later, 5 ml./Kg. of 0.4% Evance blue was injected intravenously. Another 10 minutes later, 10 ml./Kg. of 0.6% acetic acid was injected intraperitoneally. The number of writhings after 20 minutes since the administration of acetic acid was recorded and 10 minutes after that, the mice were killed by dislocation of the neck, the dye leaked in the abdominal cavity was washed out with 5 ml. of 0.9% saline to make the total amount 10 ml., and thereafter furs, blood corpuscles, etc., intermingled were removed by centrifugal separation at 3,000 r.p.m. for 5 minutes. Furthermore, for preventing turbidity caused by protein, 0.1 ml. of an aqueous 0.1 normal sodium hydroxide solution was added and then the absorbance at 590 nm was measured. The inhibition ratio of the sample administered rat groups to control groups was calculated. The results are shown in Table 2.

(c) Antipyretic effect

Male Wister rats (weighting 130–150 g.), one group being 5 rats, were used. Hyperthemia was caused by subcutaneous injection of 2 ml./rat of 20% Brewer's yeast suspension. 18 hours later, the rats showing a rise in temperature exceeding 1° C. were selected and allocated into groups each consisting of 5 rats. The sample was orally administered and then the body temperature was measured with the passage of time for 6 hours. In addition, the body temperature was measured by measuring the temperature in the rectum by means of a thermister thermometer. The results are shown in Table 3.

(d) Acute toxicity

Male Wister rats (weighting 130-170 g.), one group being 5 rats, fasted overnight were used in this test. After orally administering 500 mg./Kg. of a sample, they were observed for 7 days to determine whether they had died. The results are shown in Table 4.

In addition, the test samples used in the aforesaid tests (a), (b), (c) and (d) were prepared by suspending the test compounds, in the cases of using the compounds of Test Nos. 1,2,4,5,6,8,9,10,11,16-21 and phenylbutazone, in an aqueous 0.5% methyl cellulose solution, dissolving the test compounds, in the cases of using the compounds of Test Nos. 13,14 and 15, in aqueous solution of 0.5% methyl cellulose, and further dissolving the test compounds, in the cases of using the compounds of Test Nos. 3,7 and 12 and aminopyrine, in distilled water.

Table 1

| Test No. | $R_1$ | $R_2$ | $R_3$ | X | Y | Inhibition (%) p.o. 50mg/kg | Inhibition (%) p.o. 100mg/kg |
|---|---|---|---|---|---|---|---|
| 1 | H | –C₆H₅ | H | >N–CH₃ | –(CH₂)₃– | 71.5 | — |
| 2 | H | –C₆H₅ | H | >NH | –(CH₂)₂– | 71.6 | 76.1 |
| 3 | H | –CH₃ | H | >N–CH₃ | –(CH₂)₂– | 52.3 | 51.5 |
| 4 | H | –C₆H₅ | H | >S→O | –(CH₂)₂– | 70.2 | — |
| 5 | H | –C₆H₅ | H | >N–CH₃ | –(CH₂)₂– | 69.2 | 77.3 |
| 6 | H | –C₆H₅ | H | >NH | –(CH₂)₃– | 72.7 | 80.5 |
| 7 | –C₆H₅ | H | H | >N–CH₃ | –(CH₂)₂– | 75.0 | 79.5 |
| 8 | H | –CH₃ | H | >N–CH₃ | –(CH₂)₃– | 53.3 | — |
| 9 | H | –C₆H₅ | H | >N–C₂H₅ | –(CH₂)₂– | 51.4 | 69.8 |
| 10 | H | –C₆H₅ | H | >S | –(CH₂)₂– | — | 69.0 |
| 11 | H | –C₆H₄–Cl | H | >N–CH₃ | –(CH₂)₃– | 47.1 | — |
| 12 | H | –CH₂CH(CH₃)₂ | H | >N–CH₃ | –(CH₂)₂– | — | 72.8 |
| 13 | –(CH₂)₃– | | H | >N–CH₃ | –(CH₂)₂– | 57.1 | — |
| 14 | –(CH₂)₄– | | H | >N–CH₃ | –(CH₂)₂– | 64.1 | — |
| 15 | –(CH₂)₄– | | H | >N–CH₃ | –(CH₂)₃– | 52.4 | — |
| 16 | –C₆H₅ | –CH₃ | H | >N–CH₃ | –(CH₂)₂– | 47.7 | — |
| 17 | –CH₃ | –C₆H₅ | H | >N–CH₃ | –(CH₂)₃– | 45.7 | — |
| 18 | H | –CH₃ | –C₆H₅ | >N–CH₃ | –(CH₂)₂– | — | 41.0 |
| 19 | H | –CH₃ | –C₆H₅ | >NH | –(CH₂)₃– | — | 46.7 |
| 20 | H | –C₆H₅ | H | >NH | –CH(CH₃)–CH₂– | 72.2 | — |

Table 1-continued

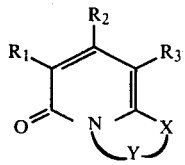

| Test No. | R₁ | R₂ | R₃ | X | Y | Inhibition (%) p.o. 50mg/kg | 100mg/kg |
|---|---|---|---|---|---|---|---|
| 21 | H | —C₆H₅ (phenyl) | H | >S | —CH=CH— | 46.9 | — |
| | | phenylbutazone | | | | 44.5 | 51.2 |

Table 2

| | Inhibition (%) | | | |
|---|---|---|---|---|
| | Writhings | | Permeability | |
| Sample | 25mg/kg p.o. | 50mg/kg p.o. | 25mg/kg p.o. | 50mg/kg p.o. |
| Compound of Test No. 1 | 41.8 | 87.6 | 18.0 | 44.4 |
| Compound of Test No. 2 | 28.9 | 52.6 | 26.9 | 51.1 |
| Compound of Test No. 3 | 52.1 | 75.3 | 18.5 | 46.2 |
| Compound of Test No. 5 | 41.2 | 67.4 | 20.0 | 42.1 |
| Compound of Test No. 6 | 69.0 | 91.5 | 28.4 | 59.0 |
| Compound of Test No. 7 | 59.1 | 95.3 | 49.3 | 63.8 |
| Compound of Test No. 8 | 35.6 | 66.4 | 32.4 | 25.8 |
| Aminopyrine | 29.6 | 58.1 | 28.5 | 41.7 |

Table 3

| Sample | Dose (p.o.) | Rectal temperature (mean ± SE) | | | | |
|---|---|---|---|---|---|---|
| | | before | 1 hour | 2 hours | 4 hours | 6 hours |
| Compound of Test No. 1 | 50mg/kg | 38.82 ± 0.05 | 37.07 ± 0.15* | 36.17 ± 0.32* | 36.12 ± 0.17* | 38.52 ± 0.47 |
| Compound of Test No. 2 | 50mg/kg | 38.89 ± 0.21 | 37.80 ± 0.10* | 36.74 ± 0.24* | 36.77 ± 0.39* | 37.51 ± 0.57* |
| Aminopyrine | 50mg/kg | 39.24 ± 0.14 | 37.92 ± 0.09 | 37.49 ± 0.10 | 37.39 ± 0.07 | 37.76 ± 0.18 |
| 0.9 % saline | 10ml/kg | 39.06 ± 0.16 | 39.56 ± 0.32 | 39.28 ± 0.23 | 39.11 ± 0.16 | 39.31 ± 0.19 |

*: significantly different from the temperature before administration ($P < 0.05$)

Table 4

| Sample No. | Number of deaths | |
|---|---|---|
| | Rat | Mouse |
| Compound of Test No. 1 | 2/5 | — |
| Compound of Test No. 2 | 0/5 | 0/5 |
| Compound of Test No. 3 | 0/5 | 1/5 |
| Compound of Test No. 4 | 2/5 | 1/5 |
| Compound of Test No. 9 | 0/5 | 0/5 |
| Compound of Test No. 10 | 0/5 | 0/5 |

From the test results by the aforesaid Carrageenin-induced edema and Wittle's method, it is clear that the compounds I of this invention have excellent anti-inflammatory activity and excellent analgesic activity. Furthermore, from the results by the antipyretic effect, it is also clear that the compounds of this invention shown by formula I have excellent antipyretic activity.

The clinical doses of the compounds I of this invention are usually 100–1,000 mg., preferably 150–600 mg. per day for an adult and the medicament is administered 2–3 times per day. The doses are properly controlled according to the condition and age of the patient.

The compounds of this invention are administered in various forms such as agents for oral administration, injections, suppositories for rectal administration, medicines for topical application, etc.

The medicaments of this invention are used as compositions prepared by blending with conventional pharmaceutical carriers or excipients by ordinary methods. The tablets, capsules, granules, powders, etc., of the compounds of this invention for oral administration may contain a pharmaceutical excipient generally used in the field of art, such as calcium carbonate, calcium phosphate, starch, sucrose, lactose, talc, magnesium stearate, gelatin, polyvinyl pyrrolidone, gum arabic, sorbitol, microcrystalline cellulose, polyethylene glycol, silica, sodium laurylsulfate, etc. Moreover, the tablets may be coated by a manner well known in the art.

Furthermore, the liquid formulations for oral administration may be an aqueous or oily suspension, a syrup, an elixir, etc., and are prepared by a conventional method.

Suppositories for rectal use are used and they may contain a formulation carrier well known in the art, such as polyethylene glycol, lanolin, cacao butter, Witepsol ® (made by Dynamite Nobel Co.), etc.

Then, examples of the formulations of the medicaments of this invention are shown below:

FORMULATION EXAMPLE 1

Tablets containing the compounds of this invention shown by formula I, the weight of one tablet being 300 mg.

Compound of formula I—1,000 g.
Lactose—1,200 g.
Starch—770 g.
Magnesium stearate—30 g.

A 10% starch paste was prepared using a part of starch described above and after adding the starch paste as a binder to a mixture of the compounds of formula I, lactose and remaining starch, the resultant mixture was granulated by a conventional manner. Then, magnesium stearate was added to the granules and the mixture was molded into 10,000 tablets each having a diameter of 9.5 mm. and weight of 300 mg. The active component was 100 mg./tablet.

FORMULATION EXAMPLE 2

Capsules containing the compounds of I of this invention, the weight of one capsule being 300 mg.
 Compound of formula I—1,000 g.
 Lactose—1,200 g.
 Starch—770 g.
 Magnesium stearate—30 g.

After mixing well 1,000 g. of the compound of formula I, 1,200 g. of lactose, 770 g. of starch, and 30 g. of magnesium stearate, the mixture was filled in 10,000 capsules. The weight of each capsule filled with the mixture was 300 mg. The active component was 100 mg./capsule.

EXAMPLE 1

In 6 ml. of xylene were refluxed 2 g. of 6-chloro-1-p-chlorophenyl-4-phenyl-2-pyridone and 2 g. of N-methylethylenediamine for 24 hours. After cooling the reaction mixture, 5 ml. of water was added to the reaction mixture, the pH thereof was adjusted to 1 by adding concentrated hydrochloric acid, and crystals thus precipitated were recovered by filtration. The crystals were washed successively with 10 ml. of ethyl acetate and 10 ml. of water and then recrystallized from 10 ml. of water to provide a crude hydrochloride salt. After adding thereto 30 ml. of water followed by heating to dissolve the hydrochloride salt, the solution was alkalified by adding sodium carbonate with stirring and then extracted twice each time with 10 ml. of chloroform. The extracts were combined, dried over anhydrous sodium sulfate, and concentrated under reduced pressure. The residue obtained was recrystallized twice from ethyl acetate to provide 0.5 g. of 1-methyl-5-oxo-7-phenyl-1,2,3,5-tetrahydroimidazo[1,2-a]pyridine.
 Melting point 159° C.
 Elemental analysis for $C_{14}H_{14}N_2O$:

|  | C | H | N |
|---|---|---|---|
| Calculated: | 74.31% | 6.24% | 12.38% |
| Found: | 74.02% | 6.09% | 12.05% |

EXAMPLE 2

In 20 ml. of 2-ethoxyethanol were refluxed 10 g. of 6-chloro-1-p-chlorophenyl-4-phenyl-2-pyridone and 5 g. of 1,3-propanediamine for 4 hours. Then, the reaction mixture was concentrated under reduced pressure and to the residue obtained were added 100 ml. of water and then concentrated hydrochloric acid to render the solution strongly acid whereby crystals were precipitated. The crystals were recovered by filtration and after washing with water, 30 ml. of methanol was added to the crystals followed by heating to dissolve the crystals. Furthermore, 30 ml. of a 10% aqueous sodium carbonate solution was added to the solution followed by stirring sufficiently, 100 ml. of water was added to the solution, and then the product was extracted with 50 ml. of chloroform. The extract was dried over anhydrous sodium sulfate and concentrated under reduced pressure to provide crude crystals. By recrystallizing twice the crude crystals from acetonitrile, 3.2 g. of 6-oxo-8-phenyl-1,2,3,4,6-pentahydropyrido[1,2-a]pyrimidine was obtained.
 Melting point 201°–203° C.
 Elemental analysis for $C_{14}H_{14}N_2O$:

|  | C | H | N |
|---|---|---|---|
| Found: | 74.21% | 6.20% | 12.49% |
| Calculated: | 74.31% | 6.24% | 12.38% |

EXAMPLE 3

In 5 ml. of 2-ethoxyethanol were refluxed 2 g. of 6-chloro-1-p-chlorophenyl-4-phenyl-2-pyridone and 1.2 g. of N-methyl-1,3-propanediamine for 50 hours. Then, by treating the reaction mixture as in Example 2, crude crystals were obtained. The crude crystals were applied to a silica gel column chromatography using 5 g. of silica gel and purified using a chloroform containing 1% methanol as an eluting solution. Furthermore, the crystals obtained were recrystallized from ethyl acetate to provide 0.42 g. of 1-methyl-6-oxo-8-phenyl-1,2,3,4,6-pentahydropyrido[1,2-a]-pyrimidine.
 Melting point 142°–143° C.
 Elemental analysis for $C_{15}H_{16}N_2O$:

|  | C | H | N |
|---|---|---|---|
| Found: | 75.13% | 6.79% | 11.91% |
| Calculated: | 74.97% | 6.71% | 11.66% |

EXAMPLE 4

In 10 ml. of 2-ethoxyethanol were refluxed 5 g. of 6-chloro-1-p-chlorophenyl-4-phenyl-2-pyridone and 3 g. of N-ethylethylenediamine for 20 hours. Then, the reaction mixture was concentrated under reduced pressure and to the residue obtained were added 30 ml. of water and then concentrated hydrochloric acid to render strong acid, whereby crystals were precipitated. The crystals were recovered by filtration and after washing with water, 15 ml. of methanol was added to the crystals followed by heating to dissolve the crystals. Then, 15 ml. of a 10% aqueous sodium carbonate solution was added to the solution and after stirring sufficiently, 50 ml. of water was added to the mixture to precipitate crystals. The crude crystals thus formed were recovered by filtration and recrystallized twice from aqueous ethyl acetate to provide 2.0 g. of 1-ethyl-5-oxo-7-phenyl-1,2,3,5-tetrahydroimidazo[1,2-a]-pyridine dihydrate.
 Melting point 83°–85° C.
 Elemental analysis for $C_{15}H_{20}N_2O_3$:

|  | C | H | N |
|---|---|---|---|
| Found: | 65.01% | 7.36% | 9.95% |
| Calculated: | 65.20% | 7.29% | 10.14% |

EXAMPLE 5

In 10 ml. of 2-ethoxyethanol were refluxed 5 g. of 6-chloro-1-p-chlorophenyl-4-phenyl-2-pyridone and 2.1 g. of ethylenediamine for 5 hours. Then, the reaction mixture was concentrated under reduced pressure and after adding 30 ml. of water to the residue obtained, concentrated hydrochloric acid was added to render the solution strongly acid, whereby crystals were precipitated. The crystals were recovered by filtration and after washing with water, 30 ml. of methanol was added to the crystals followed by heating to dissolve the crystals. Thereafter, 30 ml. of a 5% aqueous potassium carbonate solution was added to the solution followed by stirring sufficiently and then the reaction mixture was cooled. The crystals thus precipitated were recovered by filtration and recrystallized from acetonitrile to provide 1.5 g. of 5-oxo-7-phenyl-1,2,3,5-tetrahydroimidazo[1,2-a]-pyridine.

Melting point 198°–200° C.

Elemental analysis for $C_{13}H_{12}N_2O$:

|  | C | H | N |
|---|---|---|---|
| Found: | 73.72% | 5.80% | 13.53% |
| Calculated: | 73.57% | 5.70% | 13.20% |

EXAMPLE 6

In 3 ml. of 2-ethoxyethanol were refluxed 1.05 g. of 6-bromo-1-(4-methylphenyl)-4-phenyl-2-pyridone and 0.4 g. of ethylenediamine for 5 hours. Then, by treating the reaction mixture as in Example 5, 0.35 g. of 5-oxo-7-phenyl-1,2,3,5-tetrahydroimidazo[1,2-a]pyridine was obtained.

Melting point 198°–200° C.

EXAMPLE 7

In 3 ml. of 2-ethoxyethanol were refluxed 1.05 g. of 6-bromo-4-(2-chlorophenyl)-1-phenyl-2-pyridone and 0.6 g. of N-ethylethylenediamine for 27 hours. Then, by treating the reaction mixture as in Example 4, crude crystals were obtained. The crude crystals were recovered by filtration and recrystallized from ethyl acetate to provide 0.23 g. of 1-ethyl-7-(2-chlorophenyl)-5-oxo-1,2,3,5-tetrahydroimidazo-[1,2-a]pyridine.

Melting point 150°–152° C.

Elemental analysis for $C_{15}H_{15}ClN_2O$:

|  | C | H | N |
|---|---|---|---|
| Found: | 65.30% | 5.74% | 9.87% |
| Calculated: | 65.57% | 5.50% | 10.20% |

EXAMPLE 8

A mixture of 1.05 g. of 6-bromo-4-(2-chlorophenyl)-1-phenyl-2-pyridone, 0.6 g. of 1,3-propanediamine, and 3 ml. of 2-ethoxyethanol was refluxed for 4 hours. The reaction mixture obtained was concentrated and then to the residue formed were added 10 ml. of ethyl acetate and 20 ml. of a 10% aqueous hydrochloric acid solution followed by stirring sufficiently. Thereafter, the aqueous layer formed was separated, rendered alkaline by the addition of sodium carbonate, and then extracted with 20 ml. of ethyl acetate. The ethyl acetate extract was dried over anhydrous sodium sulfate and concentrated under reduced pressure. The residue obtained was applied to a column chromatography using 10 g. of silica gel and purified using chloroform as an eluting solution. The crystals obtained were recrystallized from acetonitrile to provide 0.2 g. of 8-(2-chlorophenyl)-6-oxo-1,2,3,4,6-pentahydropyrido[1,2-a]pyrimidine.

Melting point 194°–195° C. Elemental analysis for $C_{14}H_{13}N_2OCl$:

|  | C | H | N |
|---|---|---|---|
| Found: | 64.35% | 4.93% | 10.57% |
| Calculated: | 64.50% | 5.03% | 10.74% |

EXAMPLE 9

A mixture of 2 g. of 6-chloro-1-(4-chlorophenyl)-4-phenyl-2-pyridone, 2 g. of N-benzylethylenediamine, and 5 ml. of 2-ethoxyethanol was refluxed for 50 hours. Then, by treating the reaction mixture obtained as in Example 5, 0.5 g. of 1-benzyl-5-oxo-7-phenyl-1,2,3,5-tetrahydroimidazo[1,2-a]pyridine was obtained.

Melting point 165°–167° C.

Elemental analysis for $C_{20}H_{18}N_2O$:

|  | C | H | N |
|---|---|---|---|
| Found: | 79.46% | 6.14% | 9.36% |
| Calculated: | 79.44% | 6.00% | 9.26% |

EXAMPLE 10

A mixture of 2 g. of 6-chloro-1-(4-chlorophenyl)-4-phenyl-2-pyridone, 2 g. of N-cyclohexylethylenediamine, and 5 ml. of 2-ethoxyethanol was refluxed for 100 hours. The reaction mixture obtained was concentrated under reduced pressure and the residue formed was applied to a column chromatography using 30 g. of silica gel and purified using chloroform as an eluting solution. Thereafter, diluted hydrochloric acid was added to 1 g. of the oily product obtained to crystallize the product. The crystals formed were recovered and recrystallized from a mixture of acetonitrile and ethyl acetate to provide 0.5 g. of 1-cyclohexyl-5-oxo-7-phenyl-1,2,3,5-tetrahydroimidazo[1,2-a]pyridine hydrochloride.

Melting point 210°–214° C.

Elemental analysis for $C_{19}H_{23}N_2OCl$:

|  | C | H | N |
|---|---|---|---|
| Found: | 69.51% | 7.20% | 8.42% |
| Calculated: | 68.69% | 7.01% | 8.47% |

EXAMPLE 11

A mixture of 1 g. of 6-chloro-1-(4-chlorophenyl)-4-phenyl-2-pyridone, 0.7 g. of N-isopropylethylenediamine, and 2.5 ml. of 2-ethoxyethanol was refluxed for 100 hours. The reaction mixture obtained was concentrated under reduced pressure and 10 ml. of water was added to the residue thus formed. Then, the mixture was strongly acidified by the addition of concentrated hydrochloric acid to precipitate crystals. The crystals were recovered by filtration, dissolved in 10 ml. of methanol under heating, and 10 ml. of a 10% aqueous potassium carbonate solution was added to the solution followed by stirring sufficiently. Furthermore, after adding 40 ml. of water, the mixture was extracted with 20 ml. of chloroform. The chloroform extract was dried over anhydrous sodium sulfate and concentrated under reduced pressure. The residue formed was applied to a column chromatography using 5 g. of silica gel and purified using chloroform as an eluting solution. Thereafter, water was added to the oily product obtained to crystallize the product and the crystals formed were recovered and recrystallized from ether to provide 0.3 g. of 1-isopropyl-5-oxo-7-phenyl-1,2,3,5-tetrahydroimidazo[1,2-a]pyridine di-hydrate.

Melting point 74°–78° C.

EXAMPLE 12

In 15 ml. of ethylene glycol were heated 10.2 g. of 6-chloro-1-p-chlorophenyl-4-phenyl-2-pyridone and 4.6 of 2-aminoethanethiol to 200° C. for 5 hours. After the reaction was over, the reaction mixture was mixed with 100 ml. of ethyl acetate, washed three times each time with 30 ml. of 1 normal hydrochloric acid and then three times each time with 30 ml. of water, dried over anhydrous magnesium sulfate, and concentrated under reduced pressure. Then, 7.0 g. of the crude crystals obtained was applied to a silica gel column chromatography using 150 g. of silica gel and purified using a chloroform containing 1% methanol as an eluting solution. The crystals obtained were further recrystallized from ethyl acetate to provide 3.5 g. of 5-oxo-7-phenyl-2,3,5-trihydrothiazolo[3,2-a]pyridine.

Melting point 132°–134° C.

Elemental analysis for $C_{13}H_{11}NOS$:

|  | C | H | N | S |
|---|---|---|---|---|
| Found: | 68.12% | 4.84% | 6.13% | 13.61% |
| Calculated: | 68.10% | 4.84% | 6.11% | 13.98% |

EXAMPLE 13

A mixture of 0.8 g. of 6-chloro-3-phenyl-2-pyridone, 0.7 g. of N-methylethylenediamine, and 2 ml. of o-dichlorobenzene was refluxed for 5 hours. After the reaction was over, the reaction mixture was cooled and after adding thereto 10 ml. of chloroform, the mixture was washed with 5 ml. of diluted hydrochloric acid and 5 ml. of water. The chloroform layer was concentrated under reduced pressure and the residue obtained was, under shading, applied to a column chromatography using 10 g. of silica gel and purified using a chloroform containing 2% methanol as an eluting solution. The crystals obtained were recrystallized from xylene to provide 0.23 g. of 1-methyl-5-oxo-6-phenyl-1,2,3,5-tetrahydroimidazo[1,2-a]pyridine.

Melting point 128°–130° C.

Elemental analysis for $C_{14}H_{14}N_2O$:

|  | C | H | N |
|---|---|---|---|
| Calculated | 74.31% | 6.24% | 12.38% |
| Found: | 74.00% | 6.55% | 12.02% |

EXAMPLE 14

In 5 ml. of 2-ethoxyethanol were refluxed 2 g. of 6-chloro-1-(4-chlorophenyl)-4-phenyl-2-pyridone and 1.4 g. of N-(2'-hydroxyethyl)ethylenediamine for 15 hours. The reaction mixture obtained was concentrated and 10 ml. of water was added to the residue formed. Then, the pH of the mixture was adjusted to about 1 by adding concentrated hydrochloric acid to precipitate crystals, which were recovered by filtration. The crystals were recrystallized from 100 ml. of water to provide crude hydrochloride salt. The hydrochloride salt was mixed with 50 ml. of water and the mixture was alkalified by adding thereto sodium carbonate with stirring under heating. After cooling the mixture, the product was extracted twice each time with 10 ml. of chloroform. The extracts were combined, dried over anhydrous sodium sulfate, and concentrated under reduced pressure. The crystalline residue obtained was recrystallized from aqueous ethyl acetate containing activated carbon to provide 0.9 g. of 1-(2-hydroxyethyl)-5-oxo-7-phenyl-1,2,3,5-tetrahydroimidazo[1,2-a]pyridine.

Melting point 159°–161° C.

Elemental analysis for $C_{15}H_{16}N_2O_2$:

|  | C | H | N |
|---|---|---|---|
| Calculated: | 70.29% | 6.29% | 10.93% |
| Found: | 69.80% | 6.25% | 11.25% |

EXAMPLE 15

A mixture of 2.1 g. of 6-chloro-1-(4'-chlorophenyl)-4-phenyl-2-pyridone, 1.2 g. of 1,4-diaminobutane, and 6 ml. of 2-ethoxyethanol was refluxed for 40 hours. The reaction mixture obtained was concentrated under reduced pressure and the residue formed was dissolved in 20 ml. of chloroform followed by washing with 10 ml. of water. The mixture was dried over anhydrous sodium sulfate and concentrated under reduced pressure. The residue formed was applied to a silica gel column chromatography and purified using chloroform as an eluting solution to provide 0.6 g. of oily 7-oxo-9-phenyl-1,2,3,4,5,7-hexahydropyrido [1,2-a][1,3]diazepine.

Mass spectrum m/e: 240 (M+).

Nuclear magnetic resonance spectra (CHCl$_3$): δ(ppm): 1.73 (4H, m), 3.15 (2H, m), 4,32 (2H, m), 4.97 (1H, broad S), 5,93 (1H, d), 6.32 (1H, d), 7.1–7.7 (5H, m).

EXAMPLE 16

In 10 ml. of o-dichlorobenzene were dissolved 3.16 g. of 6-chloro-1-(4-chlorophenyl)-4-phenyl-2-pyridone and 1.6 g. of 1,2-diaminopropane and the solution was heated to 150°–160° C. for 20 hours using an air-cooling tube. The reaction mixture obtained was concentrated under reduced pressure and the residue obtained was mixed with water and acidified with hydrochloric acid to precipitate crystals, which were recovered by filtration. The solid product thus obtained was dissolved in methanol and after alkalifying the solution with an aqueous potassium carbonate solution, the product was extracted three times each time with 10 ml. of ethyl acetate. The extracts were combined and the solvent was distilled off under reduced pressure. The residue obtained was applied to a silica gel column chromatography and purified using a mixture of ethyl acetate and methanol as an eluting agent. The eluates containing the desired compound were collected and the solvent was distilled off. The crude crystals obtained were recrystallized from a mixture of ethyl acetate and acetonitrile to provide 1 g. of 3-methyl-5-oxo-7-phenyl-1,2,3,5-tetrahydroimidazo[1,2-a]pyridine.

Melting point 170–172° C.

Elemental analysis for $C_{14}H_{14}N_2O$:

|  | C | H | N |
|---|---|---|---|
| Calculated: | 74.31% | 6.24% | 12.38% |
| Found: | 74.12% | 6.23% | 12.17% |

EXAMPLE 17

In 10 ml. of ethanol was dissolved 280 mg. of sodium and then 1.5 g. of 2-aminopropanethiol hydrochloride was dissolved in the solution. The solution thus obtained was allowed to stand for 15 minutes at room temperature and then ethanol was distilled off under reduced pressure. The residue formed was dissolved in 10 ml. of ethylene glycol and then after adding to the solution 3.16 g. of 6-chloro-1-(4-chlorophenyl)-4-phenyl-2-pyridone, the mixture was heated to 190°–200° C. for 5 hours using an air-cooling tube. Then, the solvent was distilled off under reduced pressure from the reaction mixture and the residue obtained was extracted three times each time with 20 ml. of ethyl acetate. The extracts were combined, washed successively with 1 normal hydrochloric acid, an aqueous sodium carbonate solution, and then water, and dried over anhydrous sodium sulfate. The solvent was distilled off under reduced pressure and the residue formed was applied to a silica gel column chromatography and purified using chloroform as an eluting solution. The eluates containing the desired compound were collected and the solvent was distilled off to provide crude crystals. The crude crystals were recrystallized from a mixture of cyclohexane and ethyl acetate to provide 1.5 g. of 3-methyl-5-oxo-7-phenyl-2,3,5-trihydrothiazolo [3,2-a]pyridine.

Melting point 117°–118° C.

Elemental analysis for $C_{14}H_{13}NOS$:

|  | C | H | N | S |
|---|---|---|---|---|
| Calculated: | 69.11% | 5.39% | 5.76% | 13.18% |
| Found: | 69.16% | 5.50% | 6.08% | 13.04% |

EXAMPLE 18–40

The physical constants for Examples 18 through 40 are tabulated in Table 5. The compounds were prepared according to the procedures described in Examples 1 through 17.

Table 5

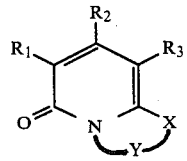

| Example | $R_1$ | $R_2$ | $R_3$ | X | Y | mp (°C.) |
|---|---|---|---|---|---|---|
| 18 | H | —C₆H₅ (phenyl) | H | >N—CH(CH₃)₂ | —(CH₂)₂— | 74–78 (di-hydrate) |
| 19 | H | —C₆H₄—OCH₃ | H | >NH | —(CH₂)₂— | 215–218 |
| 20 | H | —C₆H₄—Cl | H | >N—CH₃ | —(CH₂)₃— | 200–202 |
| 21 | H | —C₆H₄—OCH₃ | H | >N—CH₃ | —(CH₂)₃— | 138–140 (mono-hydrate) |
| 22 | H | —CH₃ | H | >N—CH₃ | —(CH₂)₂— | 144–146 |
| 23 | H | —CH₃ | H | >NH | —(CH₂)₂— | 168–169 |
| 24 | H | —CH₃ | H | >N—CH₃ | —(CH₂)₃— | 100–101 |
| 25 | H | —CH₂CH(CH₃)₂ | H | >N—CH₃ | —(CH₂)₃— | 77–78 |
| 26 | H | —CH₂CH(CH₃)₂ | H | >N—CH₃ | —(CH₂)₂— | 112–114 |
| 27 | —(CH₂)₃— |  | H | >N—CH₃ | —(CH₂)₂— | 162–163 |
| 28 | —(CH₂)₃— |  | H | >N—CH₃ | —(CH₂)₃— | 71–72 |
| 29 | —(CH₂)₄— |  | H | >N—CH₃ | —(CH₂)₂— | 111–112 |
| 30 | —(CH₂)₄— |  | H | >N—CH₃ | —(CH₂)₃— | 108–109 |
| 31 | —C₆H₅ | —CH₃ | H | >N—CH₃ | —(CH₂)₂— | 215–216 |
| 32 | —C₆H₅ | —CH₃ | H | >N—CH₃ | —(CH₂)₃— | 159–160 |

Table 5-continued

| Example | R₁ | R₂ | R₃ | X | Y | mp (°C.) |
|---|---|---|---|---|---|---|
| 33 | —$CH_3$ | —C₆H₅ (phenyl) | H | >N—$CH_3$ | —$(CH_2)_2$— | 135–136 |
| 34 | —$CH_3$ | —C₆H₅ (phenyl) | H | >N—$CH_3$ | —$(CH_2)_3$— | 114–115 (hydrochloride) |
| 35 | H | —C₆H₅ (phenyl) | H | >N—$CH_3$ | —CH—$CH_2$—<br>\|<br>$CH_3$ | 145–146 |
| 36 | —$CH_3$ | —$CH_3$ | —$CH_3$ | >NH | —$(CH_2)_2$— | 278 |
| 37 | —$CH_2$—C₆H₅ | —$CH_3$ | —C₆H₅ (phenyl) | >NH | —$(CH_2)_2$— | 239–240 |
| 38 | —$CH_2$—C₆H₅ | —$CH_3$ | —C₆H₅ (phenyl) | >N—$CH_2$—C₆H₅ | —$(CH_2)_2$— | 121–122 |
| 39 | H | —$CH_3$ | —C₆H₅ (phenyl) | >NH | —$(CH_2)_3$— | 205–206 |
| 40 | H | —C₆H₅ (phenyl) | —$CH_2$—C₆H₄—$CH_3$ | >NH | —$(CH_2)_3$— | 217–218 |

EXAMPLE 41

In 5 ml. of diglyme were refluxed 3 g. of ethyl 3-(cyanomethylene)butyrate and 1.9 g. of N-methylethylenediamine for 12 hours. The solvent was distilled off from the reaction mixture under reduced pressure and the residue formed was applied to a silica gel column chromatography and purified using a mixture of chloroform and methanol (volume ratio 49:1) as an eluting solution. The crystals formed were recrystallized from a mixture of n-hexane and ethyl acetate (volume ratio 1:1) to provide 1 g. of 1,7-dimethyl-5-oxo-1,2,3,5-tetrahydroimidazo[1,2-a]pyridine.

Melting point 144–146° C.

Elemental analysis for $C_9H_{12}N_2O$:

| | C | H | N |
|---|---|---|---|
| Calculated: | 65.83% | 7.37% | 17.06% |
| Found: | 65.54% | 7.39% | 17.14% |

EXAMPLE 42

In 5 ml. of diglyme were refluxed 3 g. of ethyl 3-(cyanomethylene)butyrate and 1.6 g. of trimethylenediamine for 12 hours under heating. The reaction mixture was poured into 30 ml. of ice water and precipitated by-products was filtered off. The filtrate was extracted three times each time with 30 ml. of chloroform and the extracts were combined and the solvent was distilled off under reduced pressure.

The liquid residue obtained was applied to a silica gel column chromatography and purified using a mixture of chloroform and methanol (volume ratio 19:1) as a eluting solution. Then, the crystals obtained were recrystallized from a mixture of cyclohexane and ethyl acetate (volume ratio 1:1) to provide 0.5 g. of 8-methyl-6-oxo-1,2,3,4,6-pentahydropyrido[1,2-a]pyrimidine.

Melting point 168°–169° C.

Elemental analysis for $C_9H_{12}N_2O$:

| | C | H | N |
|---|---|---|---|
| Calculated: | 65.83% | 7.37% | 17.06% |
| Found: | 65.92% | 7.21% | 17.25% |

EXAMPLE 43

In 5 ml. of diglyme were refluxed 3 g. of methyl 3-(cyanomethylene)butyrate and 1.9 g. of N-methyltrimethylene-diamine for 12 hours. After the reaction was over, the solvent was distilled off from the reaction mixture under reduced pressure and the liquid residue formed was applied to a silica gel column chromatography and purified using a mixture of chloroform and methanol (volume ratio 19:1) as an eluting solution. The crystals formed were recrystallized from a mixture of cyclohexane and ethyl acetate (volume ratio 1:1) to provide 1 g. of 1,8-dimethyl-6-oxo-1,2,3,4,6-pentahydropyrido[1,2-a]pyrimidine.

Melting point 100°–101° C.

Elemental analysis for $C_{10}H_{14}N_2O$:

| | C | H | N |
|---|---|---|---|
| Calculated: | 67.39% | 7.92% | 15.72% |
| Found: | 67.12% | 8.07% | 15.65% |

EXAMPLE 44

In 5 ml. of o-dichlorobenzene were dissolved 2 g. of ethyl 3-cyanomethylene-5-methylhexanoate and 1.1 g. of N-methyltrimethylenediamine and the solution was heated to 170°–180° C. for 24 hours using an air-cooling tube.

The reaction mixture was mixed with 20 ml. of benzene and extracted three times each time with 30 ml. of 1 normal hydrochloric acid. The hydrochloric acid extracts were combined, alkalified with sodium carbonate, and extracted three times each time with 30 ml. of ethyl acetate. The ethyl acetate extracts were combined, washed with water, dried over anhydrous sodium sulfate, and then the solvent was distilled off under reduced pressure.

The residue formed was recrystallized from cyclohexane to provide 250 mg. of 8-isobutyl-1-methyl-6-oxo-1,2,3,4,6-pentahydropyrido[1,2-a]pyrimidine.

Melting point 77°–78° C.
Elemental analysis for $C_{13}H_{20}N_2O$:

|  | C | H | N |
| --- | --- | --- | --- |
| Calculated: | 70.87% | 9.15% | 12.72% |
| Found: | 70.71% | 9.47% | 12.89% |

EXAMPLE 45

In 5 ml. of o-dichlorobenzene were dissolved 2 g. of ethyl 3-cyanomethylene-5-methylhexanoate and 0.9 g. of N-methylethylenediamine and the solution was heated to 170°–180° C. for 24 hours using an air-cooling tube. The reaction mixture was mixed with 20 ml. of benzene and extracted three times each time with 30 ml. of 1 normal hydrochloric acid. The hydrochloric acid extracts were combined, alkalified with sodium carbonate, and extracted three times each time with 30 ml. of chloroform. The chloroform extracts were combined, dried over anhydrous sodium sulfate, and then the solvent was distilled off under reduced pressure. The residue formed was recrystallized from cyclohexane to provide 700 mg. of 7-isobutyl-1-methyl-5-oxo-1,2,3,5-tetrahydro-imidazo-[ [1,2-a]pyridine.

Melting point 112°–114° C.
Elemental analysis for $C_{12}H_{18}N_2O$:

|  | C | H | N |
| --- | --- | --- | --- |
| Calculated: | 69.87% | 8.80% | 13.58% |
| Found: | 69.72% | 8.66% | 13.70% |

EXAMPLE 46

In 10 ml. of o-dichlorobenzene were dissolved 4.3 g. of ethyl 4-cyano-3-phenyl-3-butenoate and 1.8 g. of 2-aminoethanethiol and the solution was refluxed for 2 hours. After the reaction was over, the reaction mixture was applied to a silica gel chromatographic column using 60 g. of silica gel and purified using a chloroform containing 1% ethanol as an eluting solution. The crude crystals obtained were recrystallized from ethanol to provide 0.4 g. of 5-oxo-7-phenyl-2,3,5-trihydrothiazolo[3,2-a]pyridine.

Melting point 132°–134° C.
Elemental analysis for $C_{13}H_{11}NSO$:

|  | C | H | N | S |
| --- | --- | --- | --- | --- |
| Calculated: | 68.10% | 4.84% | 6.11% | 13.98% |
| Found: | 68.23% | 4.87% | 6.08% | 13.71% |

EXAMPLE 47

In 2 ml. of ethylene glycol were heated 0.6 g. of 3-(4-methoxyphenyl)-2-pentenedioic acid and 0.15 g. of ethylenediamine to 160°–170° C. for one hour. After coling, the reaction mixture was mixed with 20 ml. of water and the crystals precipitated were recovered by filtration and recrystallized from aqueous methanol to provide 0.12 g. of 7-(4-methoxyphenyl)-5-oxo-1,2,3,5-tetrahydroimidazo[1,2-a]pyridine.

Melting point 215°–218° C.
Elemental analysis for $C_{14}H_{14}N_2O_2$:

|  | C | H | N |
| --- | --- | --- | --- |
| Calculated: | 69.41% | 5.82% | 11.56% |
| Found: | 69.21% | 5.96% | 11.42% |

EXAMPLE 48

In 5 ml. of dichlorobenzene were refluxed 3 g. of ethyl 4-cyano-3-(4-chlorophenyl)-3-butenoate and 1.2 g. of N-methyl-1,3-propanediamine for 20 hours. The reaction mixture was concentrated under reduced pressure and the crystalline residue formed was washed with 20 ml. of ethyl acetate and recrystallized from methanol to provide 1.5 g. of 8-(4-chlorophenyl)-1-methyl-6-oxo-1,2,3,4,6-pentahydropyrido[1,2-a]pyrimidine.

Melting point 200°–202° C.
Elemental analysis for $C_{15}H_{15}N_2OCl$:

|  | C | H | N |
| --- | --- | --- | --- |
| Calculated: | 65.57% | 5.50% | 10.20% |
| Found: | 65.54% | 5.34% | 9.88% |

EXAMPLE 49

In 5 ml. of dichlorobenzene were refluxed 3 g. of ethyl 4-cyano-3-(4-methoxyphenyl)-3-butenoate and 1.2 g. of N-methyl-1,3-propanediamine for 20 hours. The reaction mixture was concentrated under reduced pressure and the crystalline residue formed was recrystallized twice from aqueous methanol to provide 1.1 g. of 8-(4-methoxyphenyl)-1-methyl-6-oxo-1,2,3,4,6-pentahydropyrido[1,2-a]pyrimidine mono-hydrate.

Melting point 138°–140° C.
Elemental analysis for $C_{16}H_{20}N_2O_3$:

|  | C | H | N |
| --- | --- | --- | --- |
| Calculated: | 66.65% | 6.99% | 9.72% |
| Found: | 67.05% | 7.05% | 9.77% |

EXAMPLE 50

A solution of 3.6 g. of a mixture of 2-cyanomethylenecyclopentane-1-carboxylic acid ethyl ester and 2-cyanomethyl-1-cyclopentene-1-carboxylic acid ethyl ester and 1.8 g. of N-methylethylenediamine in 10 ml. of o-dichlorobenzene was heated to 170°–180° C. for 24 hours with stirring using an air-cooling tube. Then, the solvent was distilled off from the reaction mixture under reduced pressure. The residue formed was applied to a silica gel chromatographic column and purified using chloroform as an eluting solution. The crystals obtained were recrystallized from ethyl acetate to provide 1.0 g. of 1-methyl-5-oxo-1,2,3,6,7,8-hexahydroimidazo[1,2-b]1H-2-pyrindine.
Melting point 162°–163° C.
Elemental analysis for $C_{11}H_{14}N_2O$:

|  | C | H | N |
|---|---|---|---|
| Found: | 69.15% | 7.16% | 14.63% |
| Calculated: | 69.45% | 7.42% | 14.72% |

EXAMPLE 51

To 10 ml. of o-dichlorobenzene containing 2.3 g. of N-methyl-1,3-diaminopropane was added 3.6 g. of a mixture of 2-cyanomethylenecyclopentane-1-carboxylic acid ethyl ester and 2-cyanomethyl-1-cyclopentene-1-carboxylic acid ethyl ester and the mixture was heated to 170°–180° C. for 24 hours with stirring using an air-cooling tube. Then, the solvent was distilled off from the reaction mixture under reduced pressure and the residue formed was applied to a silica gel chromatographic column and purified using chloroform as an eluting solution. The crystals obtained were recrystallized from a mixture of ethyl acetate and n-hexane to provide 3 g. of 1-methyl-6-oxo-1,2,3,4,7,8,9-heptahydropyrimido[1,2-b]1H-2-pyrindine.
Melting point 71°–72° C.
Elemental analysis for $C_{12}H_{16}N_2O$:

|  | C | H | N |
|---|---|---|---|
| Found: | 70.23% | 7.96% | 13.90% |
| Calculated: | 70.56% | 7.90% | 13.71% |

EXAMPLE 52

In 5 ml. of o-dichlorobenzene were dissolved 2 g. of a mixture of 2-cyanomethylene-cyclohexane-1-carboxylic acid ethyl ester and 2-cyanomethyl-1-cyclohexene-1-carboxylic acid ethyl ester (1:1) and 900 mg. of N-methylethylenediamine and the solution was heated to 170°–180° C. for 12 hours using an air-cooling tube. The reaction mixture was mixed with 20 ml. of benzene and extracted three times each time with 20 ml. of 1 normal hydrocloric acid. The hydrochloric acid extracts were combined, alkalified with sodium carbonate, and extracted three times each time with 20 ml. of ethyl acetate. The ethyl acetate extracts were combined, washed with water, and dried over anhydrous sodium sulfate. The solvent was distilled off under reduced pressure and the solid residue formed was recrystallized from cyclohexane to provide 120 mg. of 1-methyl-5-oxo-1,2,3,5,6,7,8,9-octahydroimidazo[1,2-b]isoquinoline.

Also, the benzene solution was combined with the filtrate in the recrystallization and the solution obtained was applied to a silica gel chromatographic column and purified using chloroform as an eluting solution. Then, the crystals obtained were recrystallized from cyclohexane to provide 150 mg. of 1-methyl-5-oxo-1,2,3,5,6,7,8,9-octahydroimidazo[1,2-b]isoquinoline.
Melting point 111°–112° C.
Elemental analysis for $C_{12}H_{16}ON_2$:

|  | C | H | N |
|---|---|---|---|
| Calculated: | 70.56% | 7.96% | 13.71% |
| Found: | 70.84% | 8.13% | 13.55% |

EXAMPLE 53

In 5 ml. of o-dichlorobenzene were dissolved 4 g. of a mixture of 2-cyanomethylene-cyclohexane-1-carboxylic acid ethyl ester and 2-cyanomethyl-1-cyclohexane-1-carboxylic acid ethyl ester (1:1) and 2.3 g. of N-methyl-1,3-diaminopropane and the solution was heated to 170°–180° C. for 24 hours using an air-cooling tube. From the reaction mixture, the solvent was distilled off under reduced pressure and the oily residue obtained was applied to a silica gel chromatographic column and purified using chloroform as an eluting solution. The crystals thus obtained was recrystallized from a mixture of ethyl acetate and n-hexane to provide 800 mg. of 1-methyl-6-oxo-1,2,3,4,5,6,7,8,9,10-nonahydropyrimido[1,2-b]isoquinoline.
Melting point 108°–109° C.
Elemental analysis for $C_{13}H_{18}ON_2$:

|  | C | H | N |
|---|---|---|---|
| Calculated | 71.53% | 8.31% | 12.83% |
| Found: | 71.38% | 8.55% | 12.50% |

EXAMPLE 54

In 10 ml. of o-dichlorobenzene were dissolved 4.6 g. of ethyl 4-cyano-3-methyl-2-phenyl-3-butenoate and 1.8 g. of N-methylethylenediamine and the solution was heated to 170°–180° C. for 30 hours using an air-cooling tube. Then, the reaction mixture was cooled, whereby crystals were precipitated and after adding thereto 50 ml. of ether, the crystals were recovered by filtration.

The crystals thus obtained were recrystallized from a mixture of ethyl acetate and acetonitrile to provide 2 g. of 1,7-dimethyl-5-oxo-6-phenyl-1,2,3,5-tetrahydroimidazo[1,2-a]pyridine.
Melting point 215°–216° C.
Elemental analysis for $C_{15}H_{16}ON_2$:

|  | C | H | N |
|---|---|---|---|
| Calculated: | 74.97% | 6.71% | 11.66% |
| Found: | 74.78% | 6.64% | 11.66% |

In addition, ethyl 4-cyano-3-methyl-2-phenyl-3-butenoate used as the raw material in this example was prepared by the following manner.

In 90 ml. of benzene were dissolved 62 g. of ethyl α-phenyl-acetoacetate, 27 g. of cyanoacetic acid, 5 g. of ammonium acetate, and 9 ml. of acetic acid and the solution was refluxed using a dehydrating means to provide 44 g. of ethyl 4-cyano-3-methyl-2-phenyl-3-butenoate.
Boiling point 107°–116° C./0.1 mm.Hg.
(purity about 87%).

EXAMPLE 55

In 10 ml. of o-dichlorobenzene were dissolved 4.6 g. of ethyl 4-cyano-3-methyl-2-phenyl-3-butenoate and 2.1 g. of N-methyl-1,3-diaminopropane and the solution was heated to 170°–180° C. for 20 hours using an air-cooling tube. The reaction mixture was mixed with 20 ml. of benzene and extracted three times each time with 30 ml. of a 1 normal hydrochloric acid. The hydrochloric acid extracts were combined and alkalified with sodium carbonate, whereby crystals were precipitated. The crystals were then recovered by filtration and recrystallized from xylene to provide 800 mg. of 1,8-dimethyl-6-oxo-7-phenyl-1,2,3,4,6-pentahydropyrido[1,2-a]pyrimidine.

Furthermore, the benzene solution was concentrated under reduced pressure and the residue formed was applied to a silica gel chromatographic column and purified using chloroform as an eluting solution. The solid product obtained was recrystallized from xylene to provide 450 mg. of 1,8-dimethyl-6-oxo-7-phenyl-1,2,3,4,6-pentahydropyrido[1,2-a]pyrimidine.

Melting point 159°–160° C.

Elemental analysis for $C_{16}H_{18}ON_2$:

|  | C | H | N |
|---|---|---|---|
| Calculated: | 75.56% | 7.13% | 11.01% |
| Found: | 75.47% | 7.12% | 10.96% |

EXAMPLE 56

In 10 ml. of o-dichlorobenzene were dissolved 4.6 g. of ethyl 4-cyano-2-methyl-3-phenyl-3-butenoate and 1.8 g. of N-methylethylenediamine and the solution was heated to 170°–180° C. for 24 hours using an air-cooling tube. Then, the solvent was distilled off from the reaction mixture under reduced pressure and the oily residue formed was applied to a silica gel chromatographic column and purified using chloroform as an eluting solution. The solid product obtained was recrystallized from ethyl acetate to provide 1.1 g. of 1,6-dimethyl-5-oxo-7-phenyl-1,2,3,5-tetrahydroimidazo[1,2-a]pyridine.

Melting point 135°–136° C.

Elemental analysis for $C_{15}H_{16}ON_2$:

|  | C | H | N |
|---|---|---|---|
| Calculated: | 74.97% | 6.71% | 11.66% |
| Found: | 75.10% | 6.75% | 11.57% |

In addition, ethyl 4-cyano-2-methyl-3-phenyl-3-butenoate used as the raw material in this example was prepared by the following manner.

In 130 ml. of benzene was dissolved 90 g. of ethyl α-benzoylpropionate, 39 g. of cyanoacetic acid, 7.3 g. of ammonium acetate, and 13 ml. of acetic acid and the solution was refluxed using a dehydrating means to provide 35 g. of ethyl 4-cyano-2-methyl-3-phenyl-3-butenoate.

Boiling point 101°–115° C./0.1 mm. Hg.

(purity about 80%).

EXAMPLE 57

In 10 ml. of o-dichlorobenzene were dissolved 4.69 g. of ethyl 4-cyano-2-methyl-3-phenyl-3-butenoate and 2.1 g. of N-methyl-1,3-diaminopropane and the solution was heated to 170°–180° C. for 24 hours using an air-cooling tube.

The reaction mixture was mixed with 30 ml. of benzene, washed twice each time with 20 ml. of water, dried over anhydrous sodium sulfate, and then the solvent was distilled off under reduced pressure to provide 3.9 g. of a oily residue. The residue was applied to a silica gel chromatographic column and purified using chloroform as an eluting solution, whereby 3 g. of oily 1,7-dimethyl-6-oxo-8-phenyl-1,2,3,4,6-pentahydropyrido[1,2-a]pyrimidine was obtained.

In 100 ml. of ethyl ether was dissolved 3 g. of the oily product and then 14 ml. of methanol containing 10% hydrogen chloride was added to it while stirring under ice cooling. The crystals precipitated were recovered by filtration and recrystallized from a mixture of ethyl acetate and acetonitrile to provide 1.7 g. of 1,7-dimethyl-6-oxo-8-phenyl-1,2,3,4,6-pentahydropyrido[1,2-a]pyrimidine hydrochloride.

Melting point 114°–115° C.

Elemental analysis for $C_{16}H_{19}ON_2Cl$:

|  | C | H | N | Cl |
|---|---|---|---|---|
| Calculated: | 66.09% | 6.59% | 9.63% | 12.19% |
| Found: | 66.23% | 6.62% | 9.74% | 12.22% |

EXAMPLE 58

A solution of 20 g. of ethyl 4-cyano-3-phenyl-3-butenoate and 10 g. of N-methyl-1,3-diaminopropane in 15 ml. of o-dichlorobenzene was heated to 120° C. for 2 hours and then after removing low-boiling components by distillation, the inside temperature of the system was raised to 170° C. and maintained at the same temperature for 5 hours. Then, the solution was cooled and the crystals formed were recovered by filtration, washed with 20 ml. of ethyl acetate and recrystallized from ethyl acetate to provide 9.8 g. of 1-methyl-6-oxo-8-phenyl-1,2,3,4,6-pentahydropyrido[1,2-a]pyrimidine. Melting point 143°–144° C.

EXAMPLE 59

By following the same procedure as in Example 58 using 20 g. of ethyl 4-cyano-3-phenyl-3-butenoate, 16 g. of ethylenediamine, and 15 ml. of o-dichlorobenzene, crude crystals were obtained and recrystallized from isopropanol to provide 10.5 g. of 5-oxo-7-phenyl-1,2,3,5-tetrahydroimidazo[1,2-a]pyridine.

Melting point 200°–202° C.

EXAMPLE 60–76

The physical constants for Examples 60 through 76 are tabulated in Table 6. The compounds were prepared according to the procedures described in Examples 41 through 59.

Table 6

| Ex. | $R_1$ | $R_2$ | $R_3$ | X | Y | mp(°C.) |
|---|---|---|---|---|---|---|
| 60 | H | 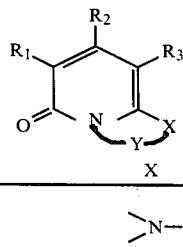 | H | $>N-CH_3$ | $-(CH_2)_2-$ | 159 |

Table 6-continued

| Ex. | R₁ | R₂ | R₃ | X | Y | mp(°C.) |
|---|---|---|---|---|---|---|
| 61 | H |  phenyl | H | >NH | —(CH₂)₃— | 201–203 |
| 62 | H |  phenyl | H | >N—C₂H₅ | —(CH₂)₂— | 83–85 (di-hydrate) |
| 63 | H |  Cl-phenyl | H | >N—C₂H₅ | —(CH₂)₂— | 150–152 |
| 64 | H |  Cl-phenyl | H | >NH | —(CH₂)₃— | 194–195 |
| 65 | H |  phenyl | H | >N—CH₂— | —(CH₂)₃— | 165–167 |
| 66 | H |  phenyl | H | >N—(S) | —(CH₂)₂— | 210–214 (hydrochloride) |
| 67 |  phenyl | H | H | >N—CH₃ | —(CH₂)₂— | 128–130 |
| 68 | H |  phenyl | H | >NH | —CH—CH₂—<br>  \|<br>  CH₃ | 170–172 |
| 69 | H |  phenyl | H | >N—CH₃ | —CH—CH₂<br>  \|<br>  CH₃ | 145–146 |
| 70 | —CH₃ | —CH₃ | —CH₃ | >NH | —(CH₂)₂— | 278 |
| 71 | —CH₂— | —CH₃ |  | >NH | —(CH₂)₂— | 239–240 |
| 72 | —CH₂— | —CH₃ |  | >N—CH₂— | —(CH₂)₂— | 121–122 |
| 73 | H | —CH₃ |  | >N—CH₃ | —(CH₂)₂— | 156–158 |
| 74 | H | —CH₃ |  | >NH | —(CH₂)₃— | 205–206 |
| 75 | H |  phenyl | H | >NH | —(CH₂)₄— | oily product(*) |
| 76 | H |  | —CH₂—⟨phenyl⟩—CH₃ | >NH | —(CH₂)₃— | 217–218 |

(*)Mass spectrum m/e: 240 (M⁺).
Nuclear magnetic resonance spectra (CHCl₃):
δ(ppm): 1.73 (4H, m), 3.15 (2H, m), 4.32 (2H, m) 4.97 (1H, broad S), 5.93 (1H, d), 6.32 (1H, d), 7.1–7.7 (5H, m)

EXAMPLE 77

To 20 ml. of methanol containing 0.3 g. of metallic sodium was added 1g. of 6-chloro-1-(2-hydroxyethyl)-4-phenyl-2-pyridone and the mixture was refluxed for 4 hours. After the reaction was over, the reaction mixture was cooled, the solvent was distilled off, and after neutralizing with 1 normal hydrochloric acid, the reaction product was extracted twice each time with 50 ml. of ethyl acetate. The extracts were combined, dried and then the solvent was distilled off.

Thereafter, the residue formed was applied to a silica gel chromatographic column and then the desired compound was separated using a mixture of chloroform and methanol as an eluting solution. The crude crystals thus obtained were recrystallized from a mixture of methanol and benzene to provide 290 mg. of 5-oxo-7-phenyl-2,3-dihydro-5H-oxazolo[3,2-a]pyridine.

Melting point 200°–203° C.
Elemental analysis for $C_{13}H_{11}NO_2$:

|  | C | H | N |
|---|---|---|---|
| Calculated: | 73.23% | 5.20% | 6.57% |
| Found: | 73.45% | 5.25% | 6.30% |

EXAMPLE 78

(a). In 10 ml. of dry benzene was dispersed 720 mg. of 50% oily sodium hydride and while refluxing the suspension under heating a solution of 3 g. of 6-chloro-4-phenyl-2-pyridone in a mixture of 20 ml. of benzene and 2 ml. of dimethylformamide was added dropwise to the suspension and thereafter, the mixture was further refluxed for 3 hours under heating. Then, after adding dropwise a solution of 2.2 g. of 3-bromopropanol in 10 ml. of benzene to the mixture, the resultant mixture was further refluxed overnight under heating. Thereafter, the reaction mixture was cooled and then extracted twice each time with 50 ml. of ethyl acetate. The extracts were combined, washed with hydrochloric acid and then water, and dried. The solvent was then distilled off under reduced pressure from the reaction mixture and the residue formed was applied to a silica gel chromatographic column and purified using a mixture of ethyl acetate and chloroform (volumn ratio 1:1) as an eluting solution to provide 1.3 g. of purified 6-chloro-1-(3-hydroxypropyl)-4-phenyl-2-pyridone.

(b). Then, 1 g. of the purified 6-chloro-1-(3-hydroxypropyl)-4-phenyl-2-pyridone was added to 15 ml. of methanol containing a slightly excessive amount of sodium methoxide and the mixture was refluxed for 1.5 hours. After the reaction was over, the reaction mixture was cooled and filtered. The solvent was distilled off from the filtrate and the residue obtained was successively washed with diluted hydrochloric acid, water, and then ethyl acetate and then recrystallized from a mixture of benzene and hexane to provide 350 mg. of 6-oxo-8-phenyl-3,4-dihydro-2H,6H-pyrido[2,1-b][1,3]oxazine.

Melting point 134°–135° C.
Elemental analysis for $C_{14}H_{13}NO_2$:

|  | C | H | N |
|---|---|---|---|
| Calculated: | 73.99% | 5.77% | 6.16% |
| Found: | 73.75% | 5.86% | 6.03% |

EXAMPLE 79–80

The physical constants for Examples 79 and 80 are tabulated in Table 7. The compounds were prepared according to the procedures described in Example 77 and 78.

Table 7.

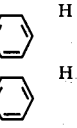

| Example | $R_1$ | $R_2$ | $R_3$ | X | Y | mp(°C.) |
|---|---|---|---|---|---|---|
| 79 | H | —⟨phenyl⟩— | H | >S | —(CH$_2$)$_2$— | 132–134 |
| 80 | H | —⟨phenyl⟩— | H | >S | —CH—CH$_2$—<br>\|<br>CH$_3$ | 117–118 |

EXAMPLE 81 in 10 ml. of acetic acid was dissolved 2.0 g. of 5-oxo-7-phenyl-2,3,5-trihydrothiazolo [3,2-a]pyridine and after adding 1.4 ml. of 30% aqueous hydrogen peroxide solution to the solution while ice-cooling, the mixture was allowed to stand overnight at room temperature. Then, after acetic acid was distilled off from the reaction mixture under reduced pressure, the residue formed was applied to a silica gel chromatographic column and purified using chloroform containing 1% ethanol as an eluting solution. Then, the crude crystals obtained were recrystallized from ethanol to provide 1.3 g. of 5-oxo-7-phenyl-2,3,5-trihydrothiazolo[3,2-a]pyridine-1-oxide.

Melting point 217°–218° C.
Elemental analysis for $C_{13}H_{11}NO_2S$:

|  | C | H | N |
|---|---|---|---|
| Found: | 63.80% | 4.54% | 5.52% |
| Calculated: | 63.66% | 4.52% | 5.71% |

EXAMPLE 82 in 4 ml. of glacial acetic acid was dissolved 460 mg. of 5-oxo-7-phenyl-2,3,5-trihydrothiazolo[3,2-a]pyridine and after adding thereto 0.5 ml. of 30% aqueous hydrogen peroxide solution, the mixture was refluxed for 2 hours. After the reaction was over, the reaction mixture obtained was cooled, mixed with 20 ml. of water, and the solid product precipitated was recovered by filtration. The precipitates thus recovered were washed with water and recrystallized from aqueous acetic acid to provide 350 mg. of 5-oxo-7-phenyl-2,3,5-trihydrothiazolo[3,2-a]pyridine-1,1-dioxide.

Melting point 233°–234° C.
Elemental analysis for $C_{13}H_{11}NO_3S$:

|  | C | H | N |
|---|---|---|---|
| Calculated: | 59.76% | 4.24% | 5.36% |
| Found: | 59.30% | 3.77% | 5.38% |

EXAMPLE 83

After adding dropwise 0.2 ml. of aqueous 30% hydrogen peroxide solution to 3 ml. of glacial acetic acid containing 165 mg. of 5-oxo-7-phenyl-5-hydrothiazolo [3,2-a]pyridine with stirring, the mixture was heated to 80° C. for 24 hours. The reaction mixture obtained was poured into 20 ml. of ice water and extracted three times each time with 10 ml. of chloroform. The extracts were combined, washed with an aqueous sodium hydrogencarbonate solution and then water, and dried over anhydrous sodium carbonate. The solvent was distilled off from the reaction mixture under reduced pressure and the residue formed was applied to a silica gel chromatographic column and purified using chloroform as an eluting solution. The eluates containing the desired compound were collected and the solvent was distilled off from the mixture. The solid product obtained was recrystallized from ethyl acetate to provide 30 mg. of 5-oxo-7-phenyl-5-hydrothiazolo [3,2-a]pyridine-1,1-dioxide.

Melting point 204°–205° C.
Elemental analysis for $C_{13}H_9NO_3S$:

|  | C | H | N |
|---|---|---|---|
| Calculated: | 60.22% | 3.50% | 5.40% |
| Found: | 59.99% | 3.56% | 5.30% |

EXAMPLE 84

In 5 ml. of glacial acetic acid was dissolved 1.2 g. of 3-methyl-5-oxo-7-phenyl-2,3,5-trihydrothiazolo [3,2-a]-pyridine and while stirring the solution under ice cooling, 0.67 ml. of 30% hydrogen peroxide solution was added dropwise to the solution. Furthermore, after stirring the mixture for 3 days at room temperature, the reaction mixture was poured into ice water and extracted three times each time with 10 ml. of ethyl acetate. The extracts were combined, washed with water, dried over anhydrous sodium sulfate, and then the solvent was distilled off under reduced pressure. The solid product thus obtained was recrystallized from a mixture of ethyl acetate and methanol to provide 400 mg. of 3-methyl-5-oxo-7-phenyl-2,3,5-trihydrothiazolo[3,2-a]pyridine-1-oxide.

Melting point 196–197° C.

Elemental analysis for $C_{14}H_{13}NO_2S$:

|  | C | H | N | S |
|---|---|---|---|---|
| Calculated: | 64.84% | 5.05% | 5.40% | 12.36% |
| Found: | 64.65% | 5.14% | 5.53% | 12.12% |

EXAMPLE 85

(a). In 5 ml. of acetic anhydride was dissolved 600 mg. of 5-oxo-7-phenyl-2,3,5-trihydrothiazolo [3,2-a]pyridine-1-oxide and after adding thereto a small amount of anhydrous sodium acetate, the mixture was refluxed for 5 hours. Then, after distilling off the reaction solvent under reduced pressure, the residue obtained was neutralized with an aqueous sodium carbonate solution and extracted three times each time with 10 ml. of chloroform. The extracts were combined, wahsed with water, dried over anhydrous sodium sulfate, and then the solvent was distilled off under reduced pressure.

(b). Then, the residue (2-acetoxy-5-oxo-7-phenyl-2,3,5-trihydrothiazolo [3,2-a]pyridine) thus obtained was mixed with 5 ml. of concentrated sulfuric acid and the mixture was allowed to stand for 30 minutes at room temperature. Thereafter, ice water was added to the mixture and the mixture was neutralized with sodium carbonate and extracted three times each time with 10 ml. of chloroform. The extracts were combined and then the solvent was distilled off under reduced pressure. The residue formed was applied to a silica gel chromatographic column and purified using chloroform as an eluting solution. The eluates containing the desired compound were collected, the solvent was distilled off, and the crystals formed were recrystallized from a mixture of cyclohexane and ethyl acetate (volume ratio 1:1) to provide 280 mg. of 5-oxo-7-phenyl-5-hydrothiazolo[3,2-a]pyridine.

Melting point 132°–133° C.

Elemental analysis for $C_{13}H_9NOS$:

|  | C | H | N |
|---|---|---|---|
| Calculated: | 68.70% | 3.99% | 6.16% |
| Found: | 68.44% | 3.70% | 6.00% |

EXAMPLE 86

(a). A mixture of 400 mg. of 3-methyl-5-oxo-7-phenyl-2,3,5-trihydrothiazolo [3,2-a]pyridine-1-oxide, 5 ml. of acetice anhydride, and a small amount of anhydrous sodium acetate was refluxed for 20 hours. The reaction mixture obtained was concentrated under reduced pressure and after adding thereto ice water, was extracted three times each time with 10 ml. of ethyl acetate. The extracts were combined, washed with water, dried over anhydrous sodium sulfate, and then the solvent was distilled off under reduced pressure.

(b). The residue (2-acetoxy-3-methyl-5-oxo-7-phenyl-2,3,5-trihydrothiazolo [3,2-a]pyridine) thus obtained was dissolved in 5 ml. of concentrated sulfuric acid and the solution was allowed to stand for 30 minutes at room temperature. Then, ice water was added to the solution and the crystals precipitated were recovered by filtration, washed with water, and recrystallized from ethyl acetate to provide 175 mg. of 3methyl-5-oxo-7-phenyl-5-hydrothiazolo[3,2-a]pyridine.

Melting point 168°–169° C.

Elemental analysis for $C_{14}H_{11}NOS$:

|  | C | H | N | S |
|---|---|---|---|---|
| Calculated: | 69.68% | 4.59% | 5.80% | 13.29% |
| Found: | 69.88% | 4.60% | 5.72% | 13.15% |

EXAMPLE 87

In a mixture of 10 ml. of ethanol and 2 ml. of water were dissolved 1.1 g. of 7-methyl-5-oxo-8-phenyl-1,2,3,5-tetrahydroimidazo [1,2-a]pyridine and 1.6 g. of potassium carbonate and then while stirring the solution, 2.5 g. of methyl iodide was added to the solution at room temperature. After stirring the mixture for 4 days at room temperature, the solvent was distilled off under reduced pressure and then the residue formed was extracted with 50 ml. of chloroform. The extract was washed with water, dried over anhydrous sodium sulfate, and then the solvent was distilled off under reduced pressure. The residue obtained was applied to a silica gel chromatographic column and purified using chloroform containing 2% methanol as an eluting solution. The crystals obtained were recrystallized from ethyl acetate to provide 350 mg. of 1,7-dimethyl-5-oxo-8-phenyl-1,2,3,5-tetrahydroimidazo [1,2-a]pyridine.

Melting point 156°–158° C.

Elemental analysis for $C_{15}H_{16}N_2O$:

|  | C | H | N |
|---|---|---|---|
| Calculated: | 74.97% | 6.71% | 11.66% |
| Found: | 74.69% | 6.67% | 11.74% |

EXAMPLE 88

To 5 ml. of methanol containing 320 mg. of 3-methyl-5-oxo-7-phenyl-1,2,3,5-tetrahydroimidazo [1,2-a]puridine and 600 mg. of methyl iodide was added 1 ml. of water containing 360 mg. of potassium carbonate and the mixture was refluxed for 7 days. After the reaction was over, the solvent was distilled off from the reaction mixture under reduced pressure and the residue formed was mixed with water, alkalified with potassium carbonate, and then extracted three times each time with 10 ml. of ethyl acetate. The extracts were combined, washed with water, and then the solvent was distilled off under reduced pressure. The residue was applied to a silica gel chromatographic column and purified using a mixture of methanol and chloroform (volume ratio 1:50) as an eluting solution. The crude crystals obtained were recrystallized from ethyl acetate to provide 120 mg. of 1,3-dimethyl-5-oxo-7-phenyl-1,2,3,5-tetrahydroimidazo-[1,2-a]pyridine.

Melting point 145°–146° C.
Elemental analysis for $C_{15}H_{16}N_2O$:

|  | C | H | N |
|---|---|---|---|
| Calculated: | 74.97% | 6.71% | 11.66% |
| Found: | 74.69% | 6.70% | 11.49% |

EXAMPLE 89

To 3 ml. of formamide were added 0.3 g. of 1,6-diamino-4-phenyl-2-pyridone and 0.2 g. of 85% formic acid and the mixture was heated to 140°–150° C. for 1 hour. The reaction mixture obtained was cooled and the crystals formed were recovered by filtration. The crystals were then recrystallized from dimethyl formamide to provide 0.15 g. of 5-oxo-7-phenyl-5-hydro-1H-1,2,4-triazolo[2,3-a]pyridine.

Melting point > 300° C.
Mass spectrum m/e: 211.
Elemental analysis for $C_{12}H_9N_3O$:

|  | C | H | N |
|---|---|---|---|
| Calculated: | 68.24% | 4.29% | 1.89% |
| Found: | 67.95% | 4.20% | 19.78% |

In addition, 1,6-diamino-4-phenyl-2-pyridone used as the raw material in this example was prepared by the following manner.

That is, in 50 ml. of ethanol was dissolved 20 g. of ethyl 4-cyano-3-phenyl-3-butenoate and after adding 7 g. of 85% hydrazine hydrate to the solution, the mixture was allowed to stand for 4 days at room temperature. The crystals precipitated were recovered by filtration to provide 10.4g. of 1,6-diamino-4-phenyl-2-pyridone.

Melting point 237°–238° C.
Elemental analysis for $C_{11}H_{11}N_3O$:

|  | C | H | N |
|---|---|---|---|
| Calculated: | 65.66% | 5.51% | 20.88% |
| Found: | 65.70% | 5.50% | 20.68% |

EXAMPL 90

To 2 ml. of dimethylformamide were added 0.3 g. of 1,6-diamino-4-phenyl-2-pyridone, 0.3 g. of acetylacetone, and 0.1 g. of p-toluenesulfonic acid and the mixture was heated to 110°–120° C. for 15 minutes. The reaction mixture obtained was cooled and crystals precipitated were recovered by filtration. The crystals thus obtained were recrystallized from dimethylformamide to provide 0.28 g. of 2-methyl-5-oxo-7-phenyl-5-hydro-1H-1,2,4-triazolo[2,3-a]pyridine.

Melting point > 300° C.
Mass spectrum m/e: 225.
Elemental analysis for $C_{13}H_{11}N_3O$:

|  | C | H | N |
|---|---|---|---|
| Calculated: | 69.32% | 4.92% | 18.65% |
| Found: | 69.33% | 5.09% | 18.59% |

EXAMPLE 91

To 10 ml. of dimethylformamide was added 0.55 g. of 2-methyl-5-oxo-7-phenyl-5-hydro-1H-1,2,4-triazolo[2,3-a]-pyridine and after adding 0.2 g. of 50% oily sodium hydride to the solution, the mixture was stirred for 10 minutes. Thereafter, 1 ml. of methyl iodide was further added and the resulting mixture was further stirred for 5 hours at room temperature. Then, the solvent was distilled off from the reaction mixture obtained under reduced pressure and then 10 ml. of water was added to the residue formed to form crude crystals. The crude crystals were washed with n-hexane and recrystallized from water with the addition of activated carbon to provide 0.25 g. of 1,2-dimethyl-5-oxo-7-phenyl-5-hydro-1,2,4-triazolo[2,3-a]pyridine.

Melting point 236°–238° C.
Mass spectrum m/e: 239.
Elemental analysis for $C_{14}H_{13}N_3O$:

|  | C | H | N |
|---|---|---|---|
| Calculated: | 70.28% | 5.48% | 17.56% |
| Found: | 70.31% | 5.39% | 17.47% |

EXAMPLE 92

To 8 ml. of dimethylformamide was added 0.45 g. of 2-methyl-5-oxo-7-phenyl-5-hydro-1H-1,2,4-triazo[2,3-a]pyridine and after adding thereto 0.2 g. of 50% oily sodium hydride, the mixture was stirred for 10 minutes. Then, 0.4 g. of benzyl bromide was added to the mixture followed by stirring for 15 hours at room temperature and then heated to 150° C. for 2 hours. The reaction mixture was mixed with 30 ml. of water and extracted with 10 ml. of chloroform. The extract was dried over anhydrous sodium sulfate and the solvent was distilled off under reduced pressure. The residue formed was applied to a silica gel chromatographic column and purified using a mixture of chloroform and methanol (volume ratio 50:1) as an eluting solution. The eluates containing the desired compound were collected and the solvent was distilled off under reduced pressure. The crystals obtained were recrystallized from aqueous ethanol to provide 0.12 of 1-benzyl-2-methyl-5-oxo-7-phenyl-5-hydro-1,2,4-triazolo[2,3-a]pyridine.

Melting point 216° C.
Mass spectrum m/e: 315.
Elemental analysis for $C_{20}H_{17}N_3O$:

|  | C | H | N |
|---|---|---|---|
| Calculated: | 76.17% | 5.43% | 13.32% |
| Found: | 75.92% | 5.39% | 12.93% |

EXAMPLE 93

To 8 ml. of o-dichlorobenzene were added 1 g. of 1,6-diamino-4-phenyl-2-pyridone and 1.2 g. of benzoylacetic acid ethyl ester and the mixture was refluxed for 4 hours. After cooling the reaction mixture, the crystals precipitated were recovered by filtration and washed with ethanol to provide crude crystals. The crude crystals were added to 30 ml. of water containing 1 g. of sodium hydroxide and after stirring for 30 minutes, insoluble materials were recovered by filtration. The insoluble materials were added to 100 ml. of water and stirred at 40°–50° C., whereby they were almost dissolved. The aqueous solution obtained was filtered and the filtrate was acidified with hydrochloric acid, whereby crystals were precipitated. The crystals were recovered by filtration and recrystallized from dimethylformamide to provide 0.23 g. of 5-oxo-2,7-diphenyl-5-hydro-1H-1,2,4-triazolo[2,3-a]-pyridine.

Melting point >300°0 C.
Mass spectrum m/e: 287.
Elemental analysis for $C_{18}H_{13}NO$:

|  | C | H | N |
|---|---|---|---|
| Calculated: | 75.25% | 4.56% | 14.62% |
| Found: | 75.08% | 4.64% | 15.06% |

EXAMPLE 94

To 3 ml. of trifluoroacetic acid was added 0.5 g. of 1,6-diamino-4-phenyl-2-pyridone and the mixture was refluxed for 20 hours. After cooling the reaction mixture thus obtained, 15 ml. of water was added thereto and crystals precipitated were recovered by filtration. The crystals were recrystallized from aqueous ethanol to provide 0.5 g. of 5-oxo-7-phenyl-2-trifluoromethyl-5-hydro-1H-1,2,4-triazolo[2,3-a]-pyridine.

Melting point 234°-236° C.
Mass spectrum m/e: 279.
Elemental analysis for $C_{13}H_8N_3OF_3$:

|  | C | H | N |
|---|---|---|---|
| Calculated: | 55.92% | 2.89% | 15.05% |
| Found: | 56.07% | 3.13% | 15.09% |

EXAMPLE 95

In 5ml. of o-dichlorobenzene were dissolved 1.9 g. of 2-cyanomethylene-cyclohexane-carboxylic acid ethyl ester and 0.93 g. of 2-aminoethanethiol and the solution was heated to 160° C. for 2 hours under stirring. Then, to the reaction mixture were added 2.0 g. of p-toluensulfonic acid followed by heating to 140°-150° C. for one hour. The reaction mixture thus obtained was concentrated under reduced pressure, then the residue was extracted with benzene. The extract was washed with 1 normal hydrochloric acid and then water, and dried over anhydrous sodium sulfate. The solvent was distilled off under reduced pressure and the residue formed was applied to a silica gel column chromatography and purified using chloroform as an eluting solution. The eluates containing the desired compound were collected and the solvent was distilled off from the mixture. The solid product obtained was recrystallized from cyclohexane to provide 500 mg. of 5-oxo-2,3,6,7,8,9-hexahydro-5H-thiazolo-[3,2-b]isoquinoline.

Melting poing 104°-105° C.
Elemental analysis for $C_{11}H_{13}NOS$:

|  | C | H | N | S |
|---|---|---|---|---|
| Calculated: | 63.74% | 6.32% | 6.76% | 15.47% |
| Found: | 63.58% | 6.39% | 6.48% | 15.45% |

EXAMPLE 96

To 15 ml. of o-dichlorobenzene were added 5.8 g. of 2-cyanomethylene-cyclohexane-carboxylic acid ethyl ester, 6.5 g. of 3-aminopropanethiol hydrobromide and 3.1 g. of sodium acetate. Then, by treating the mixture as in Example 95, 800 mg. of 6-oxo-3,4,7,8,9,10-hexahydro-2H,6H-1,3-thiazino[3,2-b]isoquinoline was obtained.

Melting point 123-124° C.
Elemental analysis for $C_{12}H_{15}NOS$:

|  | C | H | N | S |
|---|---|---|---|---|
| Calculated: | 65.12% | 6.83% | 6.33% | 14.49% |
| Found: | 64.89% | 6.85% | 6.36% | 14.32% |

EXAMPLE 97

To 15 ml. of o-dichlorobenzene were added 5.4 g. of 2-cyanomethylene-cyclopentane-carboxylic acid ethyl ester and 2.8 g of 2-aminoethanethiol. Then, by treating the mixture as in Example 95, the solid product was obtained and then it was recrystallized from ethylacetate to provide 750 mg. of 5-oxo-2,3,7,8-tetrahydro-5H,6H-thiazolo[3,2-b][2]pyrindine.

Melting point 170°-171° C.
Elemental analysis for $C_{10}H_{11}NOS$:

|  | C | H | N | S |
|---|---|---|---|---|
| Calculated: | 62.15% | 5.74% | 7.25% | 16.59% |
| Found: | 61.97% | 5.77% | 7.25% | 16.57% |

EXAMPLE 98

In 5 ml. of glacial acetic acid were dissolved 260 mg. of 5-oxo-2,3,6,7,8,9-hexahydro-5H-thiazolo[3,2-b]isoquinoline, then 0.3 ml. of 35% aqueous hydrogen peroxide solution was added to the solution, and the mixture was heated to 70°-80° C. for 2 hours. The reaction mixture was poured into water and the crystals precipitated were recovered by filteration. The crystals were then recrystallized from ethanol to provide 180 mg. of 5-oxo-2,3,6,7, 8,9-hexahydro-5H-thiazolo[3,2-b]isoquinoline-1,1-dioxide.

Melting point 230°-231° C.
Elemental analysis for $C_{11}H_{13}NO_3S$:

|  | C | H | N | S |
|---|---|---|---|---|
| Calculated: | 55.21% | 5.48% | 5.85% | 13.40% |
| Found: | 54.95% | 5.35% | 5.59% | 13.33% |

EXAMPLE 99

By following the same procedure as in Example 98 using 350 mg. of 6-oxo-3,4,7,8,9,10-hexahydro-2H, 6H-1,3-thiazole[3,2-b]isoquinoline, 5 ml. of glacial acetic acid and 0.37 ml. of 35% aqueous hydrogen peroxide solution, 10 mg. of 6-oxo-3,4,7,8,9,10-hexahydro-2H,6H-1,3-thiazino[3,2-b]isoquinoline-1,1-dioxide were obtained.

Melting point 232°-233° C.
Elemental analysis for $C_{12}H_{15}NO_3S$:

|  | C | H | N | S |
|---|---|---|---|---|
| Calculated: | 56.90% | 5.97% | 5.53% | 12.66% |
| Found: | 56.63% | 5.84% | 5.30% | 12.86% |

EXAMPLE 100

By following the same procedure as in Example 98 using 210 mg. of 5-oxo-2,3,7,8-tetrahydro-5H,6H-thiazole[3,2-b][2]pyridine, 0.5 ml. of glacial acetic acid and 0.22 ml. of 35% aqueous hydrogen peroxide solution, 150 mg. of 5-oxo-2,3,7,8-tetrahydro-5H,6H-thiazolo[3,2-b][2]pyrindine-1,1-dioxide were obtained.

Melting point 226°–227° C.

Elemental analysis for $C_{10}H_{11}NO_3S$:

|  | C | H | N | S |
|---|---|---|---|---|
| Calculated: | 53.32% | 4.92% | 6.22% | 14.23% |
| Found: | 53.04% | 4.85% | 6.00% | 13.98% |

What is claimed is:

1. A nitrogen-containing compound represented by the formula

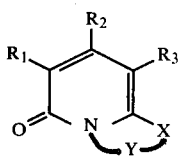

wherein one of $R_1$ and $R_2$ represents a lower alkyl group, a phenyl group, a halophenyl group, or a lower alkoxyphenyl group and the other of them represents a hydrogen atom, a lower alkyl group or a phenyl lower alkyl group; $R_3$ represents a hydrogen atom, a lower alkyl group, a phenyl group, or a phenyl lower alkyl group; X represents an imino group, or the group shown by

wherein $R_4$ represents a lower alkyl group, a hydroxy lower alkyl group, a hydroxy lower alkyl group, a cycloalkyl group, or a phenyl lower alkyl group; and Y represents an ethylene group which may be substituted by a lower alkyl group, or a vinylene group which may be substituted by a lower alkyl group; said X represents the group shown by

, when one of said $R_1$ and $R_2$ is a lower alkyl group and the other of them is a hydrogen atom, and said Y is an ethylene group, and the pharmaceutically acceptable non-toxic salts thereof.

2. A nitrogen-containing heterocyclic compound as claimed in claim 1 wherein one of $R_1$ and $R_2$ represents a lower alkyl group, a phenyl group, a halophenyl group, or a lower alkoxyphenyl group and the other of them represents a hydrogen atom or a lower alkyl group; $R_3$ represents a hydrogen atom; X represents an imino group, or the group shown by

wherein $R_4'$ represents a lower alkyl group, a cycloalkyl group, or a phenyl lower alkyl group; Y represents an ethylene group which may be substituted by a lower alkyl group, or a vinylene group which may be substituted by a lower alkyl group; said X represents a group shown by

when one of said $R_1$ and $R_2$ is a lower alkyl group and the other of them is a hydrogen atom, and said Y is an ethylene group, and the pharmaceutically acceptable non-toxic salts thereof.

3. A nitrogen-containing heterocyclic compound as claimed in claim 2 wherein $R_1$ is a hydrogen atom; $R_2$ is a phenyl group, a halophenyl group, or a lower alkoxyphenyl group; $R_3$ is a hydrogen atom; X is an imino group or the group shown by

wherein $R_4'$ has the same meaning as in claim 2; and Y is an ethylene group.

4. 1-methyl-5-oxo-7-phenyl-1,2,3,5-tetrahydroimidazo[1,2-a]pyridine as claimed in claim 3.

5. 5-oxo-7-phenyl-1,2,3,5-tetrahydroimidazo[1,2-a]pyridine as claimed in claim 3.

6. 1-ethyl-5-oxo-7-phenyl-1,2,3,5-tetrahydroimidazo[1,2-a]pyridine as claimed in claim 3.

7. A nitrogen containing heterocyclic compound as claimed in claim 2 wherein one of $R_1$ and $R_2$ is a phenyl group and the other is a hydrogen atom; $R_3$ is a hydrogen atom; X is the group shown by

wherein $R_4'$ is a lower alkyl group; and Y is an ethylene group; said X is the group shown by

when $R_1$ is a phenyl group and $R_2$ is a hydrogen atom.

8. 1-methyl-5-oxo-6-phenyl-1,2,3,5-tetrahydroimidazo[1,2-a]pyridine as claimed in claim 7.

9. A nitrogen containing heterocyclic compound as claimed in claim 2 wherein $R_1$ is a hydrogen atom; $R_2$ is a lower alkyl group; $R_3$ is a hydrogen atom; X is the group shown by

wherein $R_R'$ is a lower alkyl group; and Y is an ethylene group.

10. 1,7-dimethyl-5-oxo-1,2,3,5-tetrahydroimidazo[1,2-a]pyridine as claimed in claim 9.

11. A nitrogen containing heterocyclic compounds as claimed in claim 2 wherein one of $R_1$ and $R_2$ is a phenyl group and the other is a lower alkyl group; R₃ is a hydrogen atom; X is the group shown by

wherein (R₄' has the same meaning as in claim 2); and Y is an ethylene group.

12. 1,6-dimethyl-5-oxo-7-phenyl-1,2,3,5-tetrahydroimidazo[1,2-a]pyridine as claimed in claim 11.

13. 1,7-dimethyl-5-oxo-6-phenyl-1,2,3,5-tetrahydroimidazo[1,2-a]pyridine as claimed in claim 11.

14. A nitrogen containing heterocyclic compound as claimed in claim 2 wherein one of R₁ and R₂ is a lower alkyl group, a phenyl group, a halophenyl group or a lower alkoxyphenyl group and the other of them is hydrogen atom or a lower alkyl group, R₃ is a hydrogen atom, X is an imino group or the group shown by

wherein R₄' is a lower alkyl group, a cycloalkyl group or a phenyl lower alkyl group, Y is an ethylene group substituted by lower alkyl group or a vinylene group which may be substituted by lower alkyl group.

15. 3-methyl-5-oxo-7-phenyl-1,2,3,5-tetrahydroimidazo-[1,2-a]pyridine as claimed in claim 14.

16. 1,3-dimethyl-5-oxo-7-phenyl-1,2,3,5-tetrahydroimidazo-[1,2-a]pyridine as claimed in claim 14.

17. Analgesic anti-inflammatory composition comprising an effective amount of a compound of claim 1 and a pharmaceutically acceptable carrier or excipient.

18. A composition as claimed in claim 17 wherein said excipient is selected from the group consisting of calcium carbonate, calcium phosphate, starch, sucrose, lactose, talc, magnesium stearate, gelatin, polyvinyl pyrrolidone, gum arabic, sorbitol, microcrystalline cellulose, polyethylene glycol, silica, and sodium lauryl sulfate.

19. A composition as claimed in claim 17, in the form of an aqueous or oily suspension, a syrup, or an elixir.

20. A composition as claimed in claim 17, in the form of a suppository.

21. A method of inducing an analgesic or anti-inflammatory effect comprising administering an effective amount of the composition of claim 17.

* * * * *